(12) United States Patent
Wang et al.

(10) Patent No.: US 8,202,299 B2
(45) Date of Patent: Jun. 19, 2012

(54) INTERSPINOUS IMPLANT, TOOLS AND METHODS OF IMPLANTING

(75) Inventors: Jeffrey Chun Wang, Sherman Oaks, CA (US); Thomas Neil Scioscia, Midlothian, VA (US); Adrian Slattery, Rocky River, OH (US); Alan W. Cannon, Sunnyvale, CA (US)

(73) Assignee: Collabcom II, LLC, Durange, CO (US)

(*) Notice: Subject to any disclaimer, the term of this patent is extended or adjusted under 35 U.S.C. 154(b) by 1108 days.

(21) Appl. No.: 12/077,716

(22) Filed: Mar. 19, 2008

(65) Prior Publication Data

US 2009/0240280 A1    Sep. 24, 2009

(51) Int. Cl.
*A61B 17/70* (2006.01)
(52) U.S. Cl. ....... 606/246; 606/86 A; 606/248; 606/250; 606/99
(58) Field of Classification Search .......... 81/90.1, 81/90.6, 90.9, 420–423; 606/246–278, 90, 606/99, 105, 86 A, 86 B, 914–916, 205–211, 606/71; 623/17.16, 17.11
See application file for complete search history.

(56) References Cited

U.S. PATENT DOCUMENTS

| | | | |
|---|---|---|---|
| 891,509 A * | 6/1908 | Tanner | 81/424.5 |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,448,191 A | 5/1984 | Rodnyansky et al. | |
| 4,479,491 A | 10/1984 | Martin | |
| 4,501,269 A | 2/1985 | Babby | |
| 4,553,273 A | 11/1985 | Wu | |

(Continued)

FOREIGN PATENT DOCUMENTS

EP    1 138 268 A1    10/2001

(Continued)

OTHER PUBLICATIONS http://www.thefreedictionary.com, definition for "shaft", accessed on Oct. 3, 2011.*

(Continued)

*Primary Examiner* — Eduardo C Robert
*Assistant Examiner* — Jan Christopher Merene
(74) *Attorney, Agent, or Firm* — Alan W. Cannon

(57) ABSTRACT

Devices, tools and methods for minimally invasive implantation of a dynamic interspinous implant device for distracting between spinous processes and providing dynamic stabilization. One exemplary device includes a main body including a shaft having a longitudinal axis; a first clamping mechanism having first and second jaws configured to clamp a spinous process of a first vertebra, and a second clamping mechanism having third and fourth jaws configured to clamp a spinous process of a second vertebra. The first, second, third and fourth jaws extend transversely from the shaft and at least two of two of the jaws are releasably mounted to the shaft and are mountable to and removable from the shaft by relative movement between the respective jaw and the shaft in a direction normal to a longitudinal axis of the shaft. The shaft has sufficient columnar strength to maintain distraction between the first and second vertebrae via the clamps, while also allowing at least one of the relative movements between the first and second vertebrae selected from the movements including lateral bending, flexion, extension and axial rotation.

5 Claims, 29 Drawing Sheets

U.S. PATENT DOCUMENTS

| | | |
|---|---|---|
| 4,554,914 A | 11/1985 | Kapp et al. |
| 4,599,084 A | 7/1986 | Nashef |
| 4,599,086 A | 7/1986 | Doty |
| 4,604,995 A | 8/1986 | Stephens et al. |
| 4,611,582 A | 9/1986 | Duff |
| 4,636,217 A | 1/1987 | Ogilvie et al. |
| 4,643,178 A | 2/1987 | Nastari et al. |
| 4,653,481 A | 3/1987 | Howland et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,863,476 A | 9/1989 | Shepperd |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,030,220 A | 7/1991 | Howland |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,116,334 A | 5/1992 | Cozad et al. |
| 5,123,926 A | 6/1992 | Pisharodi |
| 5,129,899 A | 7/1992 | Small et al. |
| 5,147,359 A | 9/1992 | Cozad et al. |
| 5,154,718 A | 10/1992 | Cozad et al. |
| 5,167,662 A | 12/1992 | Hayes et al. |
| 5,180,381 A | 1/1993 | Aust et al. |
| 5,192,327 A | 3/1993 | Brantigan |
| 5,201,734 A | 4/1993 | Cozad et al. |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,330,473 A | 7/1994 | Howland |
| 5,352,225 A | 10/1994 | Yuan et al. |
| 5,387,213 A | 2/1995 | Breard et al. |
| 5,390,683 A | 2/1995 | Pisharodi |
| 5,395,370 A * | 3/1995 | Muller et al. ............... 606/276 |
| 5,395,372 A | 3/1995 | Holt et al. |
| 5,415,661 A | 5/1995 | Holmes |
| 5,443,514 A | 8/1995 | Steffee |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,534,028 A | 7/1996 | Bao et al. |
| 5,534,029 A | 7/1996 | Shima |
| 5,540,689 A | 7/1996 | Sanders et al. |
| 5,540,697 A * | 7/1996 | Rehmann et al. ............... 606/91 |
| 5,549,607 A | 8/1996 | Olson et al. |
| 5,549,679 A | 8/1996 | Kuslich |
| 5,562,736 A | 10/1996 | Ray et al. |
| 5,591,167 A * | 1/1997 | Laurain et al. ............. 606/86 A |
| 5,593,409 A | 1/1997 | Michelson |
| 5,609,634 A | 3/1997 | Voydeville |
| 5,620,444 A | 4/1997 | Assaker |
| 5,645,597 A | 7/1997 | Krapiva |
| 5,645,599 A | 7/1997 | Samani |
| 5,653,761 A | 8/1997 | Pisharodi |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,741,253 A * | 4/1998 | Michelson ............... 606/86 A |
| 5,766,252 A * | 6/1998 | Henry et al. ............... 623/17.16 |
| 5,824,098 A | 10/1998 | Stein |
| 5,836,948 A | 11/1998 | Zucherman et al. |
| 5,860,977 A | 1/1999 | Zucherman et al. |
| 5,865,846 A | 2/1999 | Bryan et al. |
| 5,876,404 A | 3/1999 | Zucherman et al. |
| 5,885,299 A | 3/1999 | Winslow et al. |
| 5,888,224 A | 3/1999 | Beckers et al. |
| 5,888,226 A | 3/1999 | Rogozinski |
| 5,928,232 A | 7/1999 | Howland et al. |
| 5,976,186 A | 11/1999 | Bao et al. |
| 5,989,250 A * | 11/1999 | Wagner et al. ............... 606/250 |
| 6,001,130 A | 12/1999 | Bryan et al. |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,155 A | 6/2000 | Michelson |
| 6,090,112 A | 7/2000 | Zucherman et al. |
| 6,113,639 A | 9/2000 | Ray et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,156,067 A | 12/2000 | Bryan et al. |
| 6,183,471 B1 | 2/2001 | Zucherman et al. |
| 6,190,387 B1 | 2/2001 | Zucherman et al. |
| 6,224,631 B1 * | 5/2001 | Kohrs ............... 623/17.11 |
| 6,234,705 B1 | 5/2001 | Troxell |
| 6,235,030 B1 | 5/2001 | Zucherman et al. |
| 6,238,397 B1 | 5/2001 | Zucherman et al. |
| 6,251,140 B1 | 6/2001 | Marino et al. |
| 6,280,444 B1 | 8/2001 | Zucherman et al. |
| 6,290,724 B1 | 9/2001 | Marino |
| 6,332,883 B1 | 12/2001 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,551,316 B1 * | 4/2003 | Rinner et al. ............... 606/57 |
| 6,652,527 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,739,068 B1 * | 5/2004 | Rinner ............... 33/783 |
| 6,761,720 B1 | 7/2004 | Senegas |
| 6,764,491 B2 * | 7/2004 | Frey et al. ............... 606/85 |
| 6,902,566 B2 | 6/2005 | Zucherman et al. |
| 6,921,403 B2 | 7/2005 | Cragg et al. |
| 7,014,633 B2 | 3/2006 | Cragg |
| 7,029,473 B2 | 4/2006 | Zucherman et al. |
| 7,029,475 B2 | 4/2006 | Panjabi |
| 7,137,985 B2 | 11/2006 | Jahng |
| 7,175,622 B2 | 2/2007 | Farris |
| 7,189,244 B2 * | 3/2007 | Newton et al. ............... 606/105 |
| 7,238,203 B2 * | 7/2007 | Bagga et al. ............... 623/17.11 |
| 7,335,203 B2 * | 2/2008 | Winslow et al. ............... 606/249 |
| 7,481,766 B2 * | 1/2009 | Lee et al. ............... 600/214 |
| 8,142,355 B2 * | 3/2012 | Blain et al. ............... 600/214 |
| 2001/0020170 A1 | 9/2001 | Zucherman et al. |
| 2002/0019633 A1 | 2/2002 | Ray |
| 2002/0077700 A1 * | 6/2002 | Varga et al. ............... 623/17.11 |
| 2002/0091446 A1 | 7/2002 | Zucherman et al. |
| 2002/0116000 A1 | 8/2002 | Zucherman et al. |
| 2003/0065330 A1 | 4/2003 | Zucherman et al. |
| 2003/0114852 A1 * | 6/2003 | Biedermann et al. ............ 606/61 |
| 2003/0139814 A1 | 7/2003 | Bryan |
| 2003/0158557 A1 | 8/2003 | Cragg et al. |
| 2003/0204189 A1 | 10/2003 | Cragg et al. |
| 2004/0153071 A1 | 8/2004 | Zucherman et al. |
| 2004/0167520 A1 | 8/2004 | Zucherman et al. |

| | | |
|---|---|---|
| 2004/0181282 A1 | 9/2004 | Zucherman et al. |
| 2004/0220568 A1 | 11/2004 | Zucherman et al. |
| 2004/0220668 A1 | 11/2004 | Eisermann et al. |
| 2004/0236331 A1 | 11/2004 | Michelson |
| 2004/0249379 A1 | 12/2004 | Winslow et al. |
| 2005/0010293 A1 | 1/2005 | Zucherman et al. |
| 2005/0010298 A1 | 1/2005 | Zucherman et al. |
| 2005/0033291 A1 | 2/2005 | Ebara |
| 2005/0075634 A1 | 4/2005 | Zucherman et al. |
| 2005/0096745 A1* | 5/2005 | Andre et al. ............... 623/17.11 |
| 2005/0125065 A1 | 6/2005 | Zucherman et al. |
| 2005/0143738 A1 | 6/2005 | Zucherman et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0216017 A1 | 9/2005 | Fielding et al. |
| 2005/0228383 A1 | 10/2005 | Zucherman et al. |
| 2005/0228384 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2006/0004447 A1 | 1/2006 | Mastrorio et al. |
| 2006/0015181 A1 | 1/2006 | Elberg |
| 2006/0036240 A1* | 2/2006 | Colleran et al. ............. 606/61 |
| 2006/0036246 A1 | 2/2006 | Carl et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0079898 A1 | 4/2006 | Ainsworth et al. |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084992 A1 | 4/2006 | Michelson |
| 2006/0085069 A1 | 4/2006 | Kim |
| 2006/0085070 A1 | 4/2006 | Kim |
| 2006/0085075 A1 | 4/2006 | McLeer |
| 2006/0089646 A1 | 4/2006 | Bonutti |
| 2006/0089654 A1 | 4/2006 | Lins et al. |
| 2006/0089718 A1 | 4/2006 | Zucherman et al. |
| 2006/0095134 A1 | 5/2006 | Trieu et al. |
| 2006/0106381 A1 | 5/2006 | Ferree et al. |
| 2006/0106397 A1 | 5/2006 | Lins |
| 2006/0122620 A1 | 6/2006 | Kim |
| 2006/0136060 A1 | 6/2006 | Taylor |
| 2006/0142760 A1 | 6/2006 | McDonnell |
| 2006/0142762 A1 | 6/2006 | Michelson |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0161154 A1 | 7/2006 | McAfee |
| 2006/0229616 A1* | 10/2006 | Albert et al. ............... 606/61 |
| 2007/0049937 A1 | 3/2007 | Matthis |
| 2007/0162000 A1 | 7/2007 | Perkins |
| 2007/0186990 A1 | 8/2007 | Serbousek |
| 2007/0233094 A1 | 10/2007 | Colleran et al. |
| 2007/0233095 A1 | 10/2007 | Schlaepfer et al. |
| 2007/0233098 A1 | 10/2007 | Mastrorio et al. |
| 2007/0239159 A1 | 10/2007 | Altarac et al. |
| 2007/0239162 A1* | 10/2007 | Bhatnagar et al. ............. 606/69 |
| 2007/0270836 A1 | 11/2007 | Bruneau et al. |
| 2007/0270837 A1 | 11/2007 | Eckhardt |
| 2007/0270838 A1 | 11/2007 | Bruneau et al. |
| 2007/0270840 A1 | 11/2007 | Chin et al. |
| 2007/0270860 A1 | 11/2007 | Jackson et al. |
| 2007/0288009 A1 | 12/2007 | Brown et al. |
| 2007/0288011 A1 | 12/2007 | Logan et al. |
| 2007/0288012 A1 | 12/2007 | Colleran et al. |
| 2007/0288014 A1 | 12/2007 | Shadduck et al. |
| 2007/0288094 A1 | 12/2007 | Krishna et al. |
| 2007/0293862 A1 | 12/2007 | Jackson et al. |
| 2007/0299445 A1 | 12/2007 | Shadduck et al. |
| 2007/0299448 A1 | 12/2007 | Chin et al. |
| 2008/0009863 A1 | 1/2008 | Bond et al. |
| 2008/0015585 A1 | 1/2008 | Berg et al. |
| 2008/0015586 A1 | 1/2008 | Krishna et al. |
| 2008/0021458 A1 | 1/2008 | Lim |
| 2008/0021459 A1 | 1/2008 | Lim |
| 2008/0021464 A1 | 1/2008 | Marin et al. |
| 2008/0021465 A1 | 1/2008 | Shadduck et al. |
| 2008/0021466 A1 | 1/2008 | Shadduck et al. |
| 2008/0262547 A1* | 10/2008 | Lewis et al. ................. 606/251 |
| 2008/0287995 A1* | 11/2008 | Gauthier ..................... 606/246 |
| 2008/0294199 A1* | 11/2008 | Kohm et al. ................. 606/248 |
| 2009/0194206 A1* | 8/2009 | Jeon et al. ................... 148/563 |
| 2009/0248079 A1* | 10/2009 | Kwak et al. ................. 606/249 |
| 2011/0238114 A1* | 9/2011 | Lim et al. ................... 606/248 |

FOREIGN PATENT DOCUMENTS

| | | |
|---|---|---|
| FR | 2 681 525 A1 | 3/1993 |
| FR | 2 707 864 A1 | 1/1995 |
| FR | 2 717 675 A1 | 9/1995 |
| FR | 2 722 980 A1 | 2/1996 |
| FR | 2 780 269 A1 | 12/1999 |
| FR | 2 782 911 A1 | 3/2000 |
| FR | 2 806 614 A1 | 9/2001 |
| FR | 2 806 616 A1 | 9/2001 |
| FR | 2 872 021 | 12/2005 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 | 4/2001 |
| WO | WO2006010844 | 2/2006 |

OTHER PUBLICATIONS

Senegas., Mechanical Supplementation by Non-Rigid Fixation in Degenerative Intervertebral Lumber Segments: The Wallis System. ( Suppl.2): S164-S169, 2002.

* cited by examiner

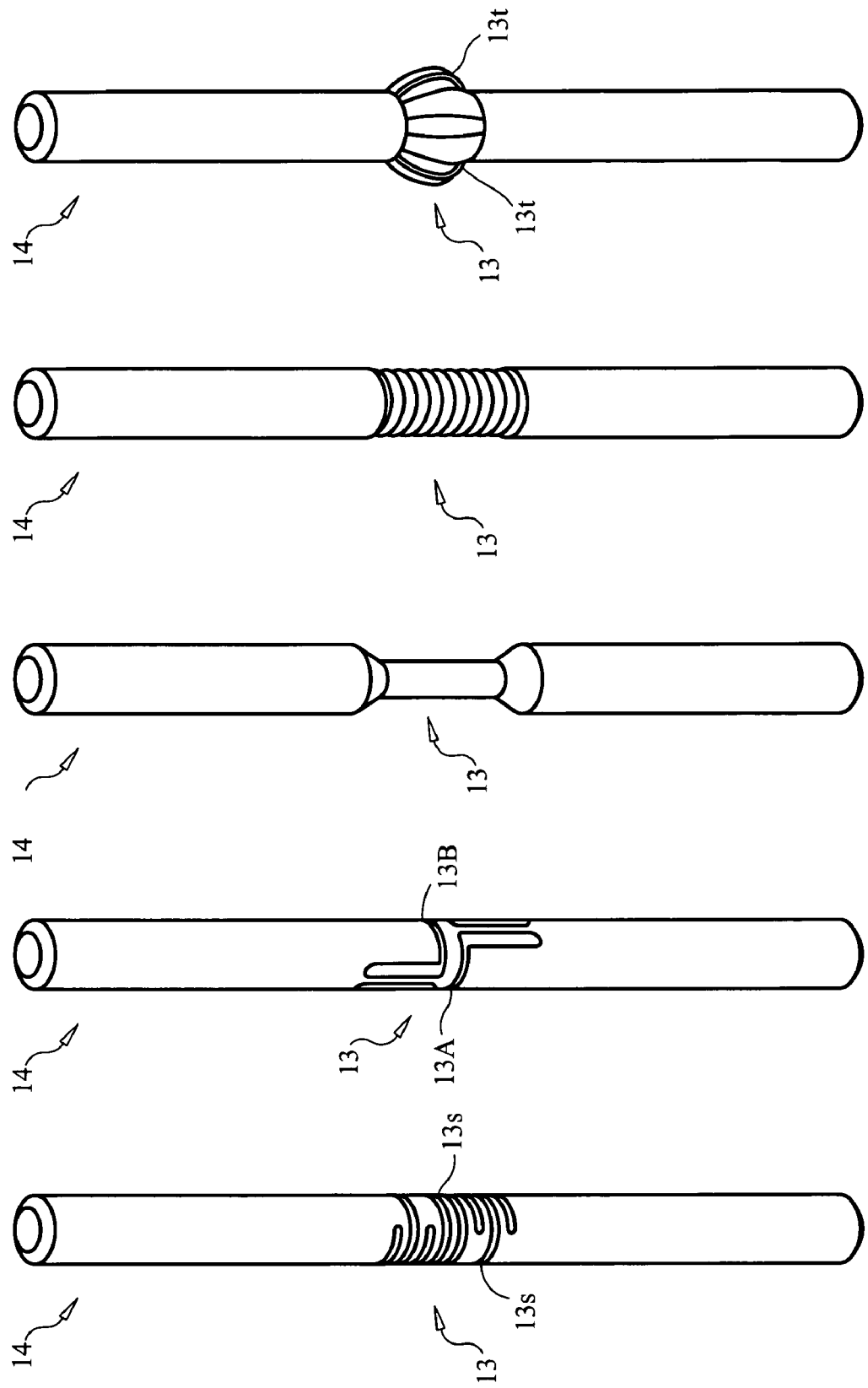

INTERSPINOUS IMPLANT, TOOLS AND METHODS OF IMPLANTING

BACKGROUND OF THE INVENTION

With the aging of the population there has occurred an increase in the incidences of degenerative diseases of the spine and this trend is expected to continue with the continuing increase in the percentage of elderly people in the population. Spinal stenosis is one of the most frequent forms of spinal degenerative disease observed. One conventional treatment of spinal stenosis has been laminectomy and decompression of compressed vertebrae and additionally fusing the treated vertebrae if instability exists. Many potentially negative side effects are inherent in this form of treatment, including profuse bleeding, substantial risk of infection, potential nerve damage sometimes leading to paralysis and/or bladder/bowel dysfunction, dural tears, persistent fluid leakage, arachnoiditis, continuing chronic pain, non-union (if fusion is performed), fusion hardware failure, donor site pain, adjacent segment disease, long operation times, and substantial operation costs.

Additionally, there are the inherent general risks of the surgical procedure and the medical risks including, but not limited to: bleeding, infection, nerve or vessel damage, risks of anesthesia, death, need for further surgery, iatrogenic instability, epidural hematoma, failure of implants and/or associated hardware, misplacement of implants and hardware, migration of implants and hardware, heart attack, stroke, deep venous thrombosis, pulmonary embolism, spinal cord and nerve damage, reflex sympathetic dystrophy, sexual dysfunction, positioning problems, brachial plexus injuries, traction injuries, swallowing difficulties, problems with vocal cords, airway obstruction, postoperative swelling, need for prolonged intubation, persistent dural fistula, paralysis, blindness, no relief of current symptoms, possible development of new symptoms, possible worsening of current symptoms, possible need for intraoperative change of procedure, possible need for fusion of the spine as determined intraoperatively, and other rare risks not named above.

Other types of implants have been developed to distract the spinous processes without the performance of laminectomy or fusion to increase the space for existing nerves to thereby relieve pain. Implantation of these implants typically require a large incision and dissection on both sides of the spinous processes. Multiple steps of dilation and distraction are performed prior to implantation of the implant in order to finally provide a sufficient interspinous space to wedge the implant between the spinous processes. Examples of implants of these types are described in U.S. Pat. Nos. 5,496,318; 5,645,599; 5,928,232; 6,149,652; 6,514,256; 6,695,842; and 6,761,720. Further, many of these devices are rigid, inflexible and/or non-adjustable wedge-like implants that require dissection of muscle tissue and/or ligaments such as the supraspinous ligament and interspinous ligament.

Other attempts have been made at providing a dynamic stabilization device, but these attempts have generally required attachment to the pedicles, which typically not only have the drawbacks associated therewith as noted above (large, bilateral incisions, etc.), but also, these types of implants compromise revision strategies when they fail. The attachment of pedicle-based dynamic stabilization can result in loosening of one or more of the pedicle screws used to attach the stabilizer to the pedicles, which can result in failure of fixation. This can preclude the salvage of pedicle screws for revision surgery and thus require more aggressive surgery. Other complications that can result from pedicle-based dynamic stabilizer arrangements include, but are not limited to: debris resulting from wear, and/or cut-out of pedicle screws into the spinal canal, which can result in neurological deterioration.

In view of these and other drawbacks with using currently existing spine treatments and inter-spinous implants, there is a continuing need for improved procedures and implants to treat disorders of the spine and pain associated therewith, and particularly for treatment of degenerative spine disorders, in the elderly as well as in any other vertebrate patients. It would be further advantageous to provide implants that are implantable via minimally invasive procedures, to reduce trauma, risks of infection and costs relative to those associated with currently available procedures. Still further, it would be desirable to provide such implants to be removable (i.e., explanted), if desired, by minimally invasive procedures. The ability to adjust the amount of distraction between the spinous processes, both during initial implantation and at a later time after completion of the implantation procedure, would also be desirable. It would also be desirable to provide devices that have the above advantages and also provide dynamic stability. It would be further desirable to provide devices that can optionally be used in a fusion procedure.

SUMMARY OF THE INVENTION

The present invention provides devices, tools and methods for minimal implantation of a dynamic interspinous implant device to placed controlled distraction between the spinous processes to increase the foraminal and thecal sac space. Devices according to the present invention can be placed with a small incision. Additionally, multi-level implants (i.e., spanning more than one disc space) can be placed, thereby greatly reducing cost and operative time when treating multiple degenerative or stenotic levels. The device can be used to apply micro-compression. This can stabilize the segment so that open micro-decompressions to alleviate the neural compression and result in stabilization of the segment with or without formal spinal fusion. Additionally or alternatively, devices described herein may be combined with fusion or can be used for degenerative disk disease treatment for stabilization of a segment alone, thereby providing dynamic stabilization. A device as described herein can stabilize a segment for fusion. Bone grafting fusions can be implanted along with the device, wherein pedicle screw fixation is not required, and the device according to the present invention maintains the stability of the segment so that bone grafting materials can fuse with the vertebral bones, thereby providing rigid stabilization. The use of flexible rods or connectors with a device of the present invention can be used for motion preservation and for fusion.

A dynamic interspinous implant device for distracting between spinous processes and providing dynamic stabilization is provided, including: a main body including a shaft having a longitudinal axis; a first clamping mechanism having first and second jaws configured to clamp a spinous process of a first vertebra; a second clamping mechanism having third and fourth jaws configured to clamp a spinous process of a second vertebra; the first, second, third and fourth jaws extending transversely from the main body, wherein at least two of the jaws are releasably mounted to the shaft and are mountable to and removable from the shaft by relative movement between the respective jaw and the shaft in a direction normal to a longitudinal axis of the shaft; and wherein the shaft has sufficient columnar strength to maintain distraction between the first and second vertebrae via the clamps, while also allowing at least one of the relative movements between the first and second vertebrae selected from the movements including lateral bending, flexion, extension, axial rotation, compression and distraction In at least one embodiment, the shaft has a length of about 30 mm to about 40 mm for a single-level application, typically about 35 mm, with lengths for two-level applications being about double the length of the single-level application rod and lengths for three-level applications being about triple the lengths of the single-level application rods, etc., for lumbar applications. These lengths will vary for placements in different locations of the spine and will also vary depending upon the patient anatomy, sex, whether adult or pediatric, etc. For example, a shaft having a length of about 30 mm to about 40 mm, typically about 35 mm may be used for certain single-level cervical applications. The devices of the present invention may further be used to treat more than three adjacent levels, wherein the number of levels treated is equal to the number of intervertebral (disc) spaces being treated.

In at least one embodiment, each releasably mounted jaw comprises a threaded boss extending from a proximal end portion of the respective jaw, each threaded boss comprising a recess configured to receive the shaft.

In at least one embodiment, a threaded nut is configured to mate with each threaded boss, respectively, wherein, after receiving the shaft in the recess, the nut is torquable over the threaded boss and against the shaft to fix the jaw to the shaft.

In at least one embodiment, the shaft comprises slots cut into a central portion thereof.

In at least one embodiment, the shaft comprises a necked-down, central portion having a cross section less than a cross section first and second end portions of the shaft.

In at least one embodiment, the shaft comprises a solid rod at first and second end portions, and a helical spring configuration at a central portion thereof.

In at least one embodiment, the shaft comprises a central portion having deformable, compliant struts.

In at least one embodiment, the shaft allows all of the relative movements between the first and second vertebrae comprising: lateral bending, flexion, extension and axial rotation.

In at least one embodiment, at least one jaw of each the clamp comprises a dog-leg shaped portion to allowing mounting the jaws of the clamp closer together on the shaft.

In at least one embodiment, a second shaft having a longitudinal axis is provided, the second shaft being mountable to at least two of the jaws at distal end portions thereof, so that the second shaft is mounted on a side of the spinal processes that is opposite a side of the spinal processes that the first shaft is mounted on.

In at least one embodiment, the first and second shafts allow at least one of the relative movements between the first and second vertebrae selected from the movements including flexion and extension.

In at least one embodiment, each of the at least two jaws that the second shaft is mountable to comprises a threaded boss extending from a distal end portion thereof, the threaded boss comprising a recess configured to receive the second shaft.

In at least one embodiment, a threaded nut is configured to mate with each threaded boss, respectively, wherein, after receiving the second shaft in the recess, the nut is torquable over the threaded boss and against the second shaft to fix the respective jaw to the second shaft.

In at least one embodiment, the second shaft is mountable to all of the first, second, third and fourth jaws.

In at least one embodiment, each of the jaws comprises an engagement feature configured to be engaged by an insertion tool configured to insert the jaws into a target surgical area.

A tool for inserting jaws of clamping mechanisms of a dynamic interspinous implant device is provided, including: an insertion arm having a distal end with a rotatable engagement feature configured to pass through a mating engagement feature on one of the jaws, and to be prevented from passing through the mating engagement feature after rotations of the rotatable engagement feature; and a locking arm actuatable to rotate the rotatable engagement feature.

In at least one embodiment, the tool includes two insertion arms and two locking arms.

In at least one embodiment, a pair of drive arms are provided at a proximal end portion of the tool connected via a pivotal mount to the insertion arms and operable to drive the insertion arms toward each other and away from one another.

A tool for compressing jaws of clamping mechanisms of a dynamic interspinous implant device so as to securely clamp spinous processes is provided, wherein the tool includes: first and second compressor arms having first and second distal tips formed with recesses configured and dimensioned to receive a shaft of the implant device therein; and a pair of drive arms at a proximal end portion of the tool connected via a pivotal mount to the compressor arms and operable to drive the compressor arms toward each other when driving the drive arms toward each other.

A tool for distracting clamping mechanisms of a dynamic interspinous implant device away from one another is provided, wherein the tool includes: first and second distractor arms having first and second distal tips formed with recesses configured and dimensioned to receive a shaft of the implant device therein; and a pair of drive arms at a proximal end portion of the tool connected via a pivotal mount to the distractor arms and operable to drive the distractor arms away from each other when driving the drive arms toward each other.

A method of treating spinal disorders and associated discomfort therefrom, the method including: inserting a first jaw of a first clamping mechanism through an interspinous ligament superiorly of a first spinous process; inserting a second jaw of the first clamping mechanism through the interspinous ligament inferiorly of the first spinous process; inserting a third jaw of a second clamping mechanism through the interspinous ligament superiorly of a second spinous process; inserting a fourth jaw of the second clamping mechanism through the interspinous ligament inferiorly of the second spinous process; attaching a shaft to the jaws; clamping the first and second jaws against the first spinous process and locking relative positions of the first and second jaws relative to the shaft in a clamped configuration; distracting the first and second spinous processes to a distracted configuration; and locking relative positions of the third and fourth jaws relative to the shaft in a clamped configuration; wherein the shaft has sufficient columnar strength to maintain distraction between the first and second vertebrae via the clamps, while also allowing at least one of the relative movements between the first and second vertebrae selected from the movements including lateral bending, flexion, extension and axial rotation.

In at least one embodiment, the distracting comprises distracting the second and third jaws apart from one another, and wherein the locking the third and fourth jaws in a clamped configuration comprises first locking the third jaw upon performance of the distracting, and the compressing the fourth jaw toward the third jaw to clamp the second spinous process and locking the fourth jaw.

In at least one embodiment, the shaft comprises a first shaft, and the method further includes: attaching a second shaft to at least two of the jaws prior to the clamping, so that the jaws are still slidable relative to the second shaft; and locking the at least two jaws relative to the second shaft when the at least two jaws are locked relative to the first shaft.

In at least one embodiment, the attaching a second shaft to at least two of the jaws comprises attaching the second shaft to all of the first, second, third and fourth jaws.

A method of treating spinal disorders and associated discomfort therefrom, is provided, including: inserting a first jaw of a first clamping mechanism through an interspinous ligament superiorly of a first spinous process; inserting a second jaw of the first clamping mechanism through the interspinous ligament inferiorly of the first spinous process; inserting a third jaw of a second clamping mechanism through the interspinous ligament superiorly of a second spinous process; inserting a fourth jaw of the second clamping mechanism through the interspinous ligament inferiorly of the second spinous process; attaching a shaft to the jaws; clamping the first and second jaws against the first spinous process and locking relative positions of the first and second jaws relative to the shaft in a clamped configuration; micro-compressing the first and second spinous processes by compressing the fourth jaw toward the second jaw and locking the fourth jaw relative to the shaft in a micro-compressed configuration; compressing the third jaw toward the fourth jaw to clamp the second spinous process; and locking the third jaw in a clamped configuration; wherein the shaft has sufficient columnar strength to maintain distraction between the first and second vertebrae via the clamps, while also allowing at least one of the relative movements between the first and second vertebrae selected from the movements including lateral bending, flexion, extension and axial rotation.

In at least one embodiment, the shaft comprises a first shaft, the method further comprising: attaching a second shaft to at least two of the jaws prior to the clamping, so that the jaws are still slidable relative to the second shaft; and locking the at least two jaws relative to the second shaft when the at least two jaws are locked relative to the first shaft.

In at least one embodiment, the attaching a second shaft to at least two of the jaws comprises attaching the second shaft to all of the first, second, third and fourth jaws.

A kit for treatment of spinal disorders is provided, including: a device including: a main body including a shaft having a longitudinal axis; a first clamping mechanism having first and second jaws configured to clamp a spinous process of a first vertebra; a second clamping mechanism having third and fourth jaws configured to clamp a spinous process of a second vertebra; the first, second, third and fourth jaws extending transversely from the main body, wherein at least two of the jaws are releasably mounted to the shaft and are mountable to and removable from the shaft by relative movement between the respective jaw and the shaft in a direction normal to a longitudinal axis of the shaft; and wherein the shaft has sufficient columnar strength to maintain distraction between the first and second vertebrae via the clamps, while also allowing at least one of the relative movements between the first and second vertebrae selected from the movements including lateral bending, flexion, extension and axial rotation; and a tool for inserting jaws of the clamping mechanisms, the tool including: an insertion arm having a distal end with a rotatable engagement feature configured to pass through a mating engagement feature on one of the jaws, and to be prevented from passing through the mating engagement feature after rotations of the rotatable engagement feature; and a locking arm actuatable to rotate the rotatable engagement feature.

In at least one embodiment, the kit further includes a tool for compressing jaws of the clamping mechanisms, the tool for compressing comprising: first and second compressor arms having first and second distal tips formed with recesses configured and dimensioned to receive the shaft therein; and a pair of drive arms at a proximal end portion of the tool for compressing connected via a pivotal mount to the compressor arms and operable to drive the compressor arms toward each other when driving the drive arms toward each other.

In at least one embodiment, the kit further includes a tool for distracting the clamping mechanisms, the tool comprising: first and second distractor arms having first and second distal tips formed with recesses configured and dimensioned to receive a shaft of the implant device therein; and a pair of drive arms at a proximal end portion of the tool connected via a pivotal mount to the distractor arms and operable to drive the distractor arms away from each other when driving the drive arms toward each other.

A method of treating spinal disorders and associated discomfort therefrom is provided, including: inserting a first jaw of a first clamping mechanism through an interspinous ligament superiorly of a first spinous process; inserting a second jaw of the first clamping mechanism through the interspinous ligament inferiorly of the first spinous process; inserting a third jaw of a second clamping mechanism through the interspinous ligament superiorly of a second spinous process; inserting a fourth jaw of the second clamping mechanism through the interspinous ligament inferiorly of the second spinous process; attaching a shaft to the jaws; clamping the first and second jaws against the first spinous process and locking relative positions of the first and second jaws relative to the shaft in a clamped configuration; performing one of: distracting the first and second spinous processes to a distracted configuration or micro-compressing or micro-compressing the first and second spinous processes by compressing to a micro-compressed configuration; locking relative positions of the third and fourth jaws relative to the shaft in a clamped configuration; wherein the shaft together with the locked jaws form a device that maintains the distracted or micro-compressed configuration; and placing a bone ingrowth enhancement agent in contact with at least a portion of both of the adjacent vertebrae and a least a portion of the device.

In at least one embodiment, the placing comprises delivering the agent on one lateral side of the adjacent vertebrae and device.

In at least one embodiment, the placing comprises delivering the agent on both lateral sides of the adjacent vertebrae and device.

In at least one embodiment, the placing comprises delivering a slurry of bone-ingrowth enhancing material to the vertebrae and device.

In at least one embodiment, the spinous processes are not altered.

In at least one embodiment, the supraspinous ligament is maintained intact between the spinous processes.

An interspinous implant device for distracting between spinous processes or micro-compressing the spinous processes to facilitate a fusion procedure is provided, including: a main body including a shaft having a longitudinal axis; a first clamping mechanism having first and second jaws configured to clamp a spinous process of a first vertebra; a second clamping mechanism having third and fourth jaws configured to clamp a spinous process of a second vertebra; the first, second, third and fourth jaws extending transversely from the main body, wherein at least two of the jaws are releasably mounted to the shaft and are mountable to and removable from the shaft by relative movement between the respective jaw and the shaft in a direction normal to a longitudinal axis of the shaft; and a bone ingrowth enhancing agent.

In at least one embodiment, a second shaft having a longitudinal axis is provided, the second shaft being mountable to at least two of the jaws at distal end portions thereof, so that the second shaft is mounted on a side of the spinal processes that is opposite a side of the spinal processes that the first shaft is mounted on.

A kit for treatment of spinal disorders is provided, including: a device having: a main body including a shaft having a longitudinal axis; a first clamping mechanism having first and second jaws configured to clamp a spinous process of a first vertebra; a second clamping mechanism having third and fourth jaws configured to clamp a spinous process of a second vertebra; the first, second, third and fourth jaws extending transversely from the main body, wherein at least two of the jaws are releasably mounted to the shaft and are mountable to and removable from the shaft by relative movement between the respective jaw and the shaft in a direction normal to a longitudinal axis of the shaft; and a component for facilitating fusion of the adjacent vertebrae while the device is implanted between the spinous processes.

In at least one embodiment, the device of the kit further includes a second shaft having a longitudinal axis, the second shaft being mountable to at least two of the jaws at distal end portions thereof, so that the second shaft is mounted on a side of the spinal processes that is opposite a side of the spinal processes that the first shaft is mounted on.

These and other features of the invention will become apparent to those persons skilled in the art upon reading the details of the devices, tools and methods as more fully described below.

BRIEF DESCRIPTION OF THE DRAWINGS

FIGS. 6A-6E show alternative embodiments of a shaft according to the present invention.

DETAILED DESCRIPTION OF THE INVENTION

Before the present devices, tools, systems and procedures are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an inter-spinous space" includes a plurality of such inter-spinous spaces and reference to the "nut" includes reference to one or more nuts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Vertebral Anatomy

Figure 1:
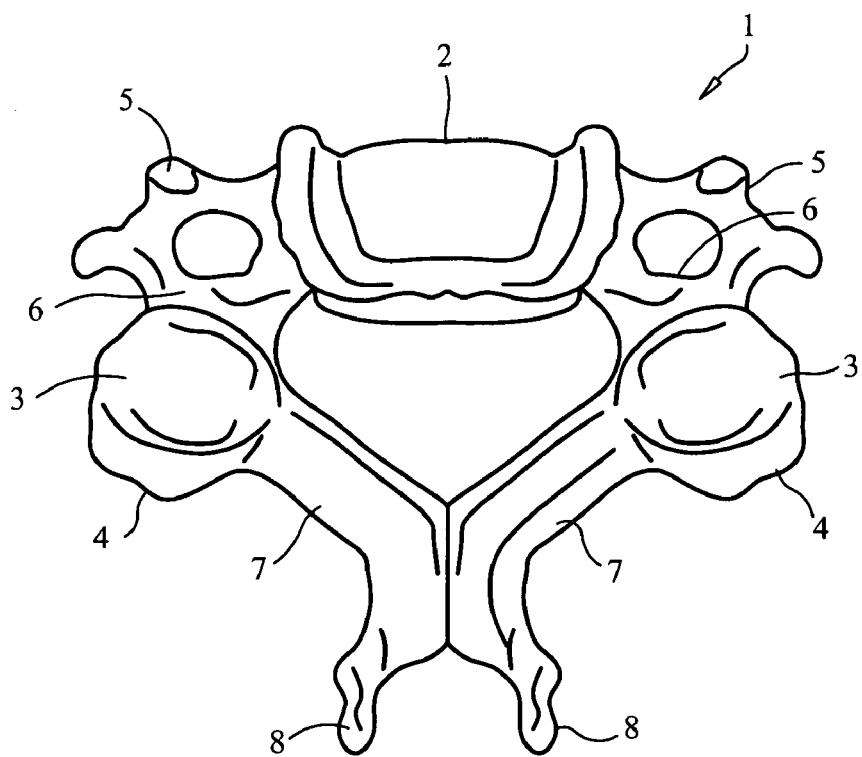
FIG. 1 is a superior view of a vertebra.

FIG. 1 is a superior view of a vertebra 1. The vertebral body 2 is an anterior portion of the vertebra and is somewhat cylindrical in shape. The intervertebral disks (not shown) are interposed between adjacent vertebral bodies in the spine.

Each vertebra has two sets of facet joints 3,4, at posterior locations. One pair faces upward (superior articular facets 3) and one downward (inferior articular facets 4). There is one joint on each side (right and left). Facet joints are hinge-like and link vertebrae together. A transverse process 5 and pedicle 6 are located between the facets 3,4 and the vertebral body 2. The transverse processes 5 serve for the attachment of muscles and ligaments. The laminae 7 are plates of bone that form the posterior walls of each vertebra 2, enclosing the spinal cord. The spinous process 8 is directed backward and downward from the junction of the laminae 7, and serves for the attachment of muscles and ligaments.

Figure 2:
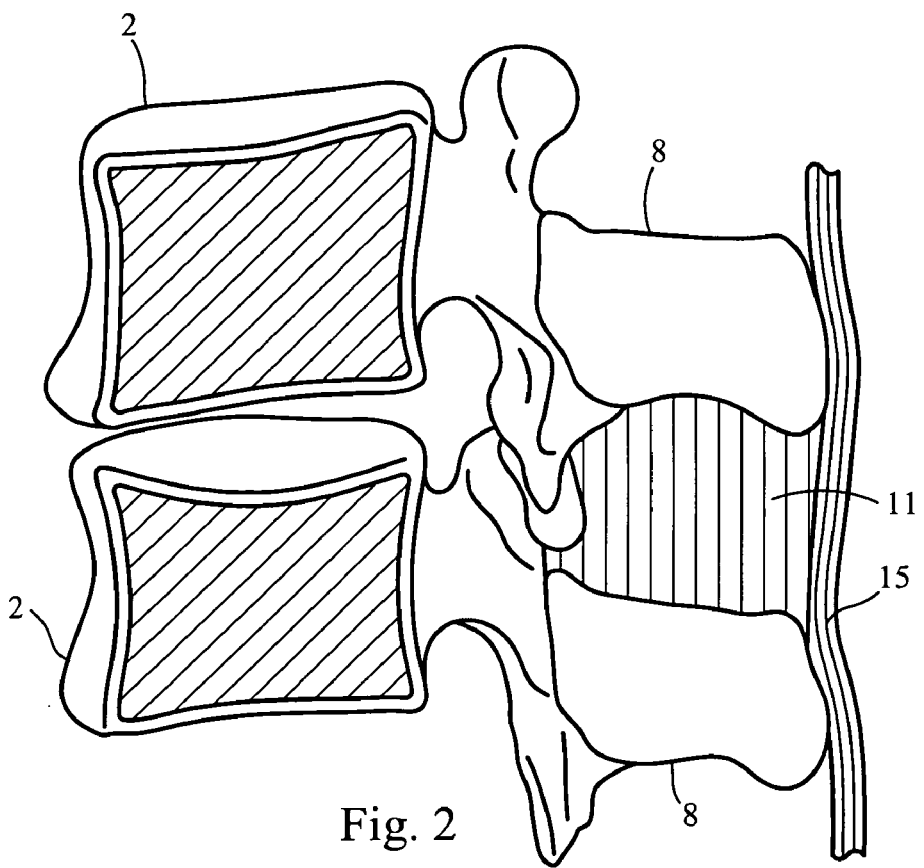
FIG. 2 is an illustration showing a lateral view of adjacent spinous processes 8,8 and a sectional view of the vertebral bodies 2 from the lumbar portion of the spine.

FIG. 2 is an illustration showing a lateral view of adjacent spinous processes 8,8 and a sectional view of the vertebral bodies 2 from the lumbar portion of the spine. FIG. 2 further illustrates interspinous ligament 11 and supraspinous ligament 15. Interspinous ligament 11 connects the adjacent spinous processes and stretches vertically from the inferior border of the upper spinous process 8 shown to the superior border of the adjacent spinous process 8 below. Interspinous ligament 11 interconnects adjacent spinous processes 8 in this manner with respect to all vertebrae, except those in the cervical spine, where it is absent. Supraspinous ligament 15 extends along the posterior tips of the spinous processes 8 and blends with the ligamentum nuchae at its superior end. In elderly individuals and in persons who engage in heavy physical activity, the ligament can become ossified, making a midline approach to the epidural space impossible.

Devices, Tools, Systems and Procedures

Figure 3A:
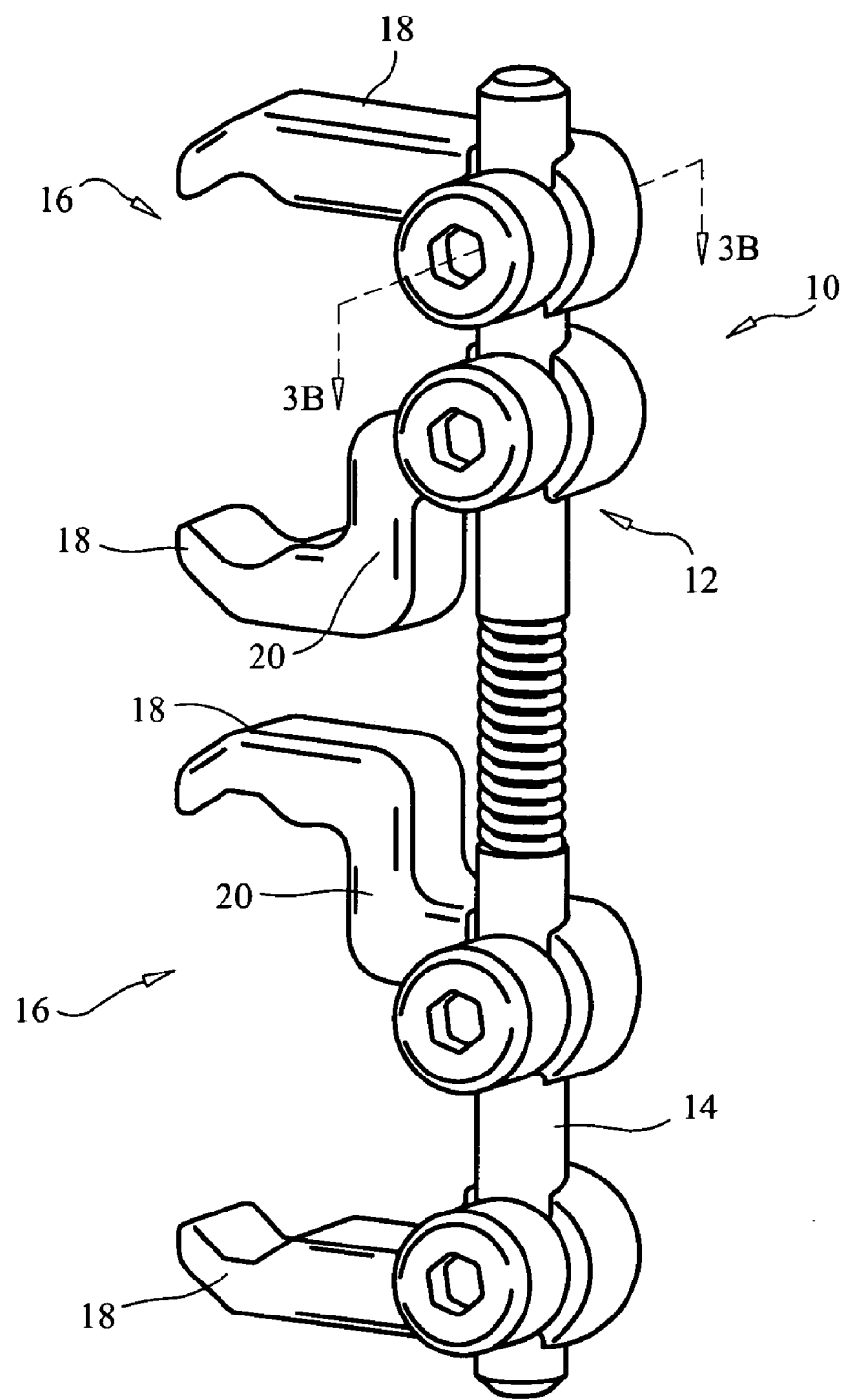
FIG. 3A shows an embodiment of a unilateral dynamic interspinous implant device according to the present invention.

FIG. 3A shows an embodiment of a dynamic interspinous implant device 10 according to the present invention. Device 10 includes a main body 12. Main body 12 includes a shaft 14 and clamping mechanisms 16 mounted thereto. Each clamping mechanism 16 includes a pair of jaws 16 extending transversely with respect to shaft 14, as shown in FIG. 3A. Optionally, and as shown in FIG. 3A at least one jaw of each pair of jaws in a clamping mechanism may include a dog-leg shaped portion to move the attachment locations of the jaw pairs closer together on shaft 14 thereby leaving greater space for the dynamic central portion 13 of the shaft 14, which is described in greater detail below.

Jaws 18 are configured and dimensioned to pass over and under a spinous process 8 so that opposite jaws 18 of a clamping mechanism can be clamped against superior and inferior portions of the spinous process, respectively. The jaws and connecting hardware may be made of titanium, cobalt chromium alloy, or other rigid, biocompatible metals or alloys. Shaft 14 is formed from one or more materials that provide with sufficient column strength to maintain a desired distraction between spinous processes 8 (and thus vertebrae) that are clamped by clamping mechanisms 16 after the jaws 18 or clamping mechanisms 16 have been fixed relative to shaft 14 to prevent relative movement between any of jaws 18 and shaft 14. As such, shaft 14 may be made of a relatively stiff polymer that still allows some bending and twisting to take place, such as PEEK (polyetheretherketone), for example. Alternatively, the end portions of the shaft 14 may be made of a rigid material, such as a biocompatible rigid metal, polymer, alloy or composite, and the central portion only can then be made more compliant to allow for bending or twisting and bending. The arrangement shown in FIG. 3A allows limited flexion, extension, axial rotation and bending of the vertebrae that are connected by device 10. A typical length of shaft 14 for a one-level device 10 as shown in FIG. 3A, when used in a cervical spine location, is in the range of about 30 mm to about 50 mm, or about 35 mm to about 45 mm, and, in at least one embodiment, about 40 mm; when used in a thoracic spine location is about 35 mm to about 65 mm, or about 40 mm to about 60 mm, and, in at least one embodiment, about 50 mm, and when used in a lumbar spine location, is in the range of about 40 mm to about 80 mm, or about 50 mm to about 70 mm, and, in at least one embodiment, is about 60 mm. For two level devices, when used in a cervical spine location, shaft 14 is in the range of about 40 mm to about 60 mm, when used in a thoracic spine location is in the range of about 55 mm to about 80 mm, and when used in a lumbar spine location, is in the range of about 70 mm to about 100 mm. For three level devices, when used in a cervical spine location, the length of shaft 14 is in the range of about 50 mm to about 70 mm, when used in a thoracic spine location is about 75 mm to about 100 mm, and when used in a lumbar spine location, is in the range of about 100 mm to about 140 mm. These lengths may further vary depending upon the anatomy of a particular patient, for example, as well as other factors.

Figure 3B:
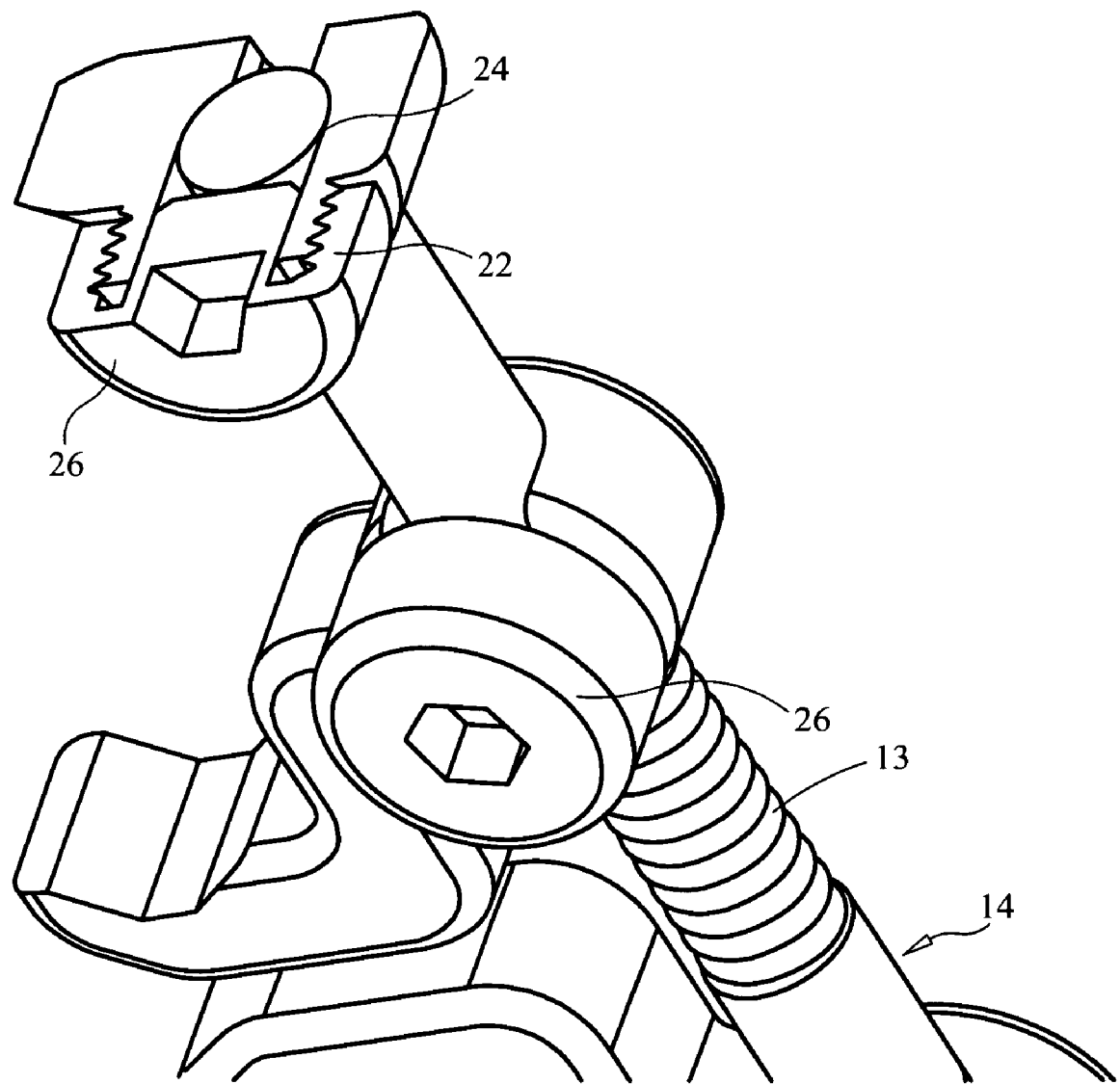
FIG. 3B is a cutaway view of FIG. 3A taken along line 3B-3B.
Figure 3C:
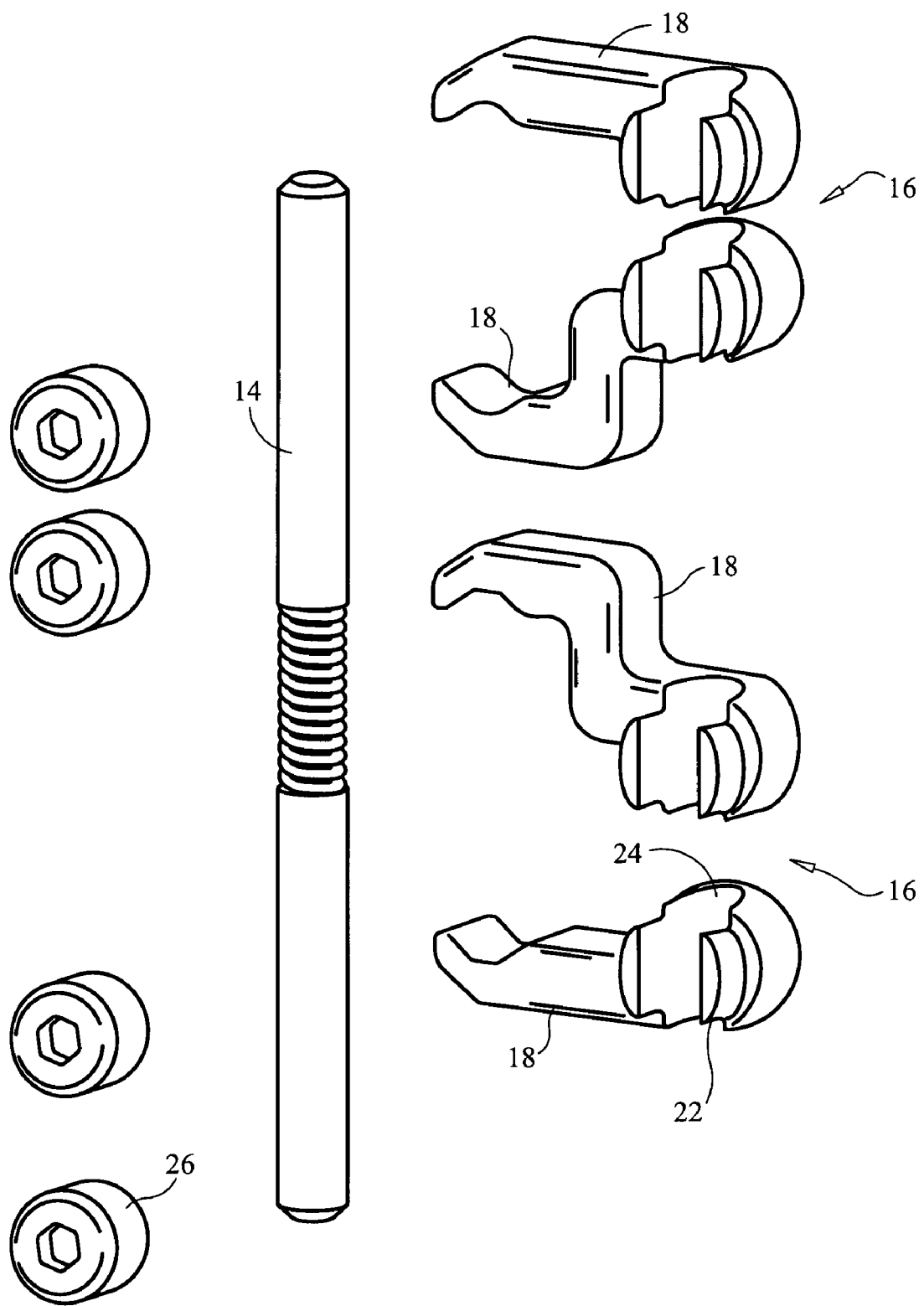
FIG. 3C shows an exploded view of the device of FIG. 3A.

Jaws 18 are attached to shaft 14. At least the intermediate jaws (e.g., lower jaw 18 of the upper clamping mechanism 16 and upper jaw 18 of the lower clamping mechanism 16 shown in FIG. 3A) are releasably connected to shaft 14 in a manner that the shaft 14 and jaws 18 are removable, as well as connectable (mountable) by relative movement between the respective jaw 18 and the shaft 14 in a direction normal to a longitudinal axis of the shaft 14. This is made possible by providing the proximal end portion of each such jaw 16 with a threaded boss 22 extending transversely to the longitudinal axis of the jaw. Each threaded boss has a recess 24, as illustrated in the cutaway view of FIG. 3B, configured to receive the shaft 14. Once the shaft 14 is received in the recess 24, a threaded nut or cap 26 having threads that mate with the threads on boss 22, can be threaded onto the boss 22. This may first be done by a loose connection, which connects the jaw 18 to the shaft 14, but still allows relative sliding between the components, and then the nut 26 may be further torqued to lock the jaw relative to the shaft to prevent relative sliding therebetween as discussed in greater detail below. FIG. 3C shows an exploded view of the device 10 of FIG. 3A, for increased clarity of visualization of the components.

FIG. 3A shows an embodiment of a dynamic interspinous implant device 10 according to the present invention. Device 10 includes a main body 12. Main body 12 includes a shaft 14 and clamping mechanisms 16 mounted thereto. Each clamping mechanism 16 includes a pair of jaws 16 extending transversely with respect to shaft 14, as shown in FIG. 3A. Optionally, and as shown in FIG. 3A at least one jaw of each pair of jaws in a clamping mechanism may include a dog-leg shaped portion to move the attachment locations of the jaw pairs closer together on shaft 14 thereby leaving greater space for the dynamic central portion 13 of the shaft 14, which is described in greater detail below.

Jaws 18 are configured and dimensioned to pass over and under a spinous process 8 so that opposite jaws 18 of a clamping mechanism can be clamped against superior and inferior portions of the spinous process, respectively. The jaws and connecting hardware may be made of titanium, chromium cobalt, or other rigid, biocompatible metals. Shaft 14 is formed from one or more materials that provide with sufficient column strength to maintain a desired distraction between spinous processes 8 (and thus vertebrae) that are clamped by clamping mechanisms 16 after the jaws 18 or clamping mechanisms 16 have been fixed relative to shaft 14 to prevent relative movement between any of jaws 18 and shaft 14. As such, shaft 14 may be made of a relatively stiff polymer that still allows some bending and twisting to take place, such as PEEK (polyetheretherketone), for example. Alternatively, the end portions of the shaft 14 may be made of a rigid material, such as a biocompatible rigid metal, polymer, alloy or composite, and the central portion only can then be made more compliant to allow for bending or twisting and bending. The arrangement shown in FIG. 3A allows limited flexion, extension, axial rotation and bending of the vertebrae that are connected by device 10. A typical length of shaft 14 for a one level device 10 as shown in FIG. 3A, when used in a cervical spine location, may be in the range of about 30 mm to about 50 mm, when used in a thoracic spine location may be about 35 mm to about 60 mm, and when used in a lumbar spine location, may be in the range of about 40 mm to about 80 mm, although these ranges may vary. For two level devices, when used in a cervical spine location, the length of shaft 14 may be in the range of about 40 mm to about 60 mm, when used in a thoracic spine location may be about 55 mm to about 80 mm, and when used in a lumbar spine location, is in the range of about 70 mm to about 100 mm, although these ranges may vary. For three level devices, when used in a cervical spine location, the length of shaft 14 may be in the range of about 50 mm to about 70 mm, when used in a thoracic spine location may be about 75 mm to about 100 mm, and when used in a lumbar spine location, may be in the range of about 100 mm to about 140 mm, although these ranges may vary.

Jaws 18 are attached to shaft 14. At least the intermediate jaws (e.g., lower jaw 18 of the upper clamping mechanism 16 and upper jaw 18 of the lower clamping mechanism 16 shown in FIG. 3A) are releasably connected to shaft 14 in a manner that the shaft 14 and jaws 18 are removable, as well as connectable (mountable) by relative movement between the respective jaw 18 and the shaft 14 in a direction normal to a longitudinal axis of the shaft 14. This is made possible by providing the proximal end portion of each such jaw 16 with a threaded boss 22 extending transversely to the longitudinal axis of the jaw. Each threaded boss has a recess 24, as illustrated in the cutaway view of FIG. 3B, configured to receive the shaft 14. Once the shaft 14 is received in the recess 24, a threaded nut or cap 26 having threads that mate with the threads on boss 22, can be threaded onto the boss 22. This may first be done by a loose connection, which connects the jaw 18 to the shaft 14, but still allows relative sliding between the components, and then the nut 26 may be further torqued to lock the jaw relative to the shaft to prevent relative sliding therebetween as discussed in greater detail below. FIG. 3C shows an exploded view of the device 10 of FIG. 3A, for increased clarity of visualization of the components.

Figure 4A:
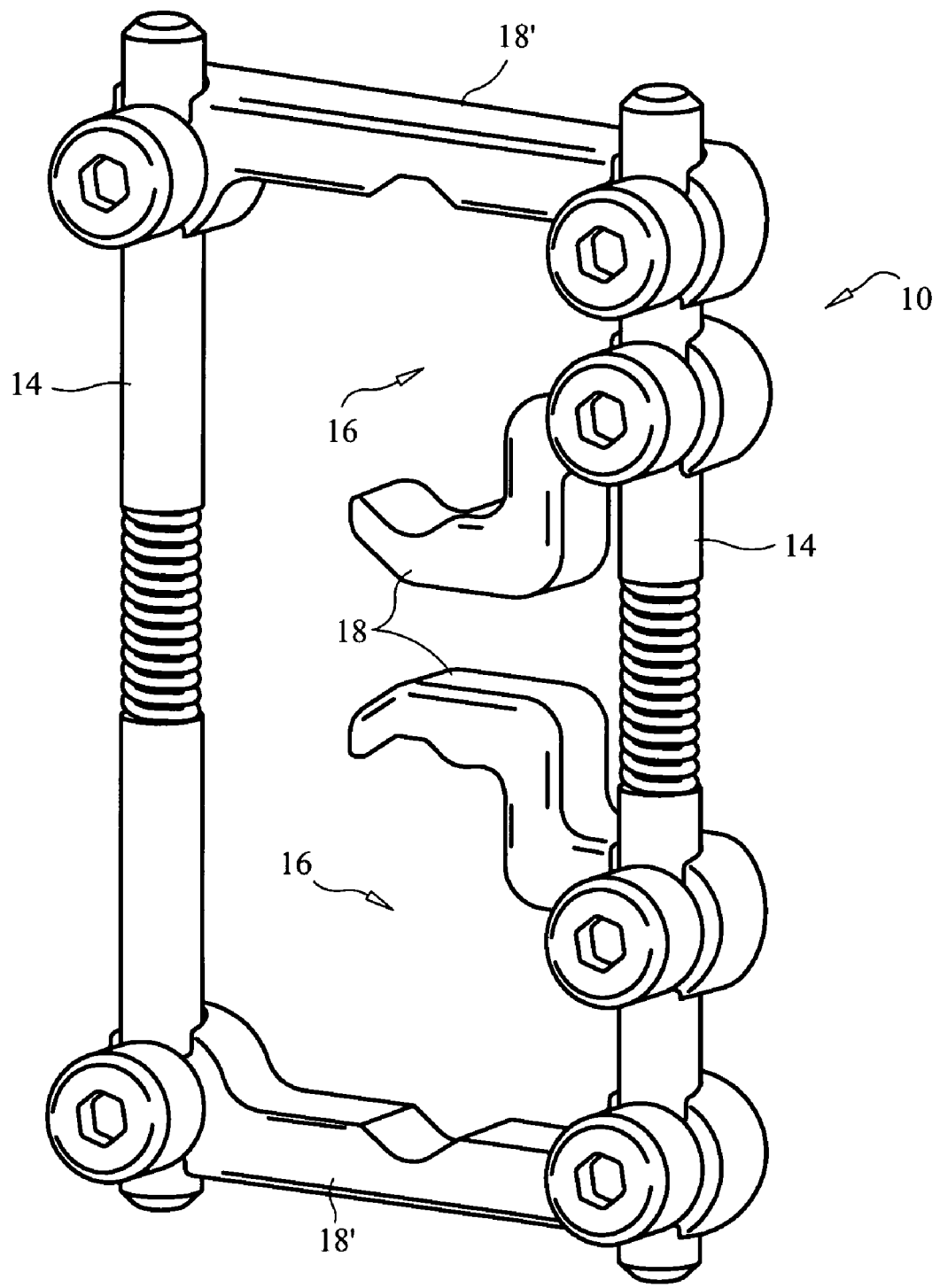
FIG. 4A shows an embodiment of a bilateral dynamic interspinous implant device according to the present invention.
Figure 4B:
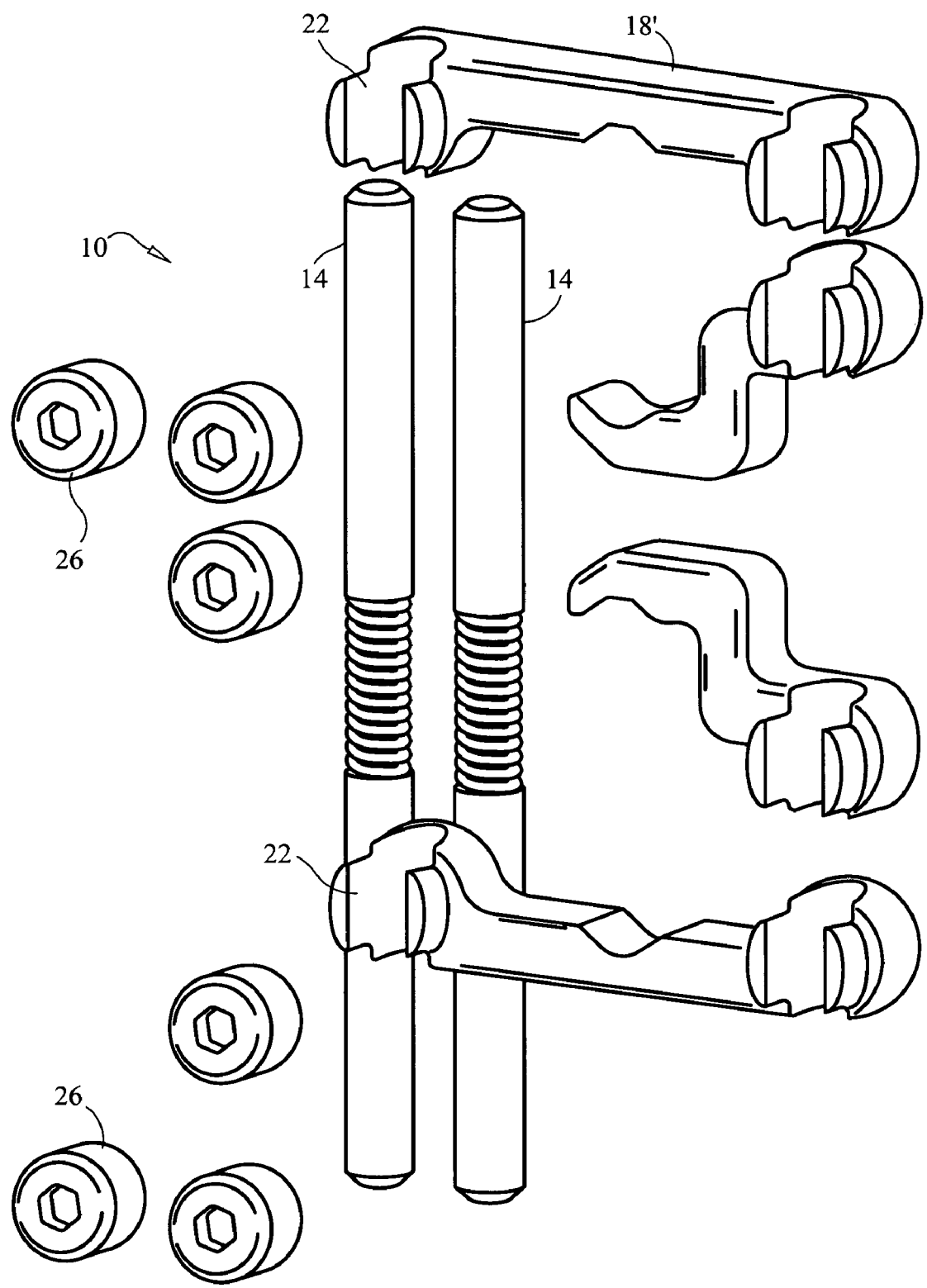
FIG. 4B shows an exploded view of the device of FIG. 4A.

FIG. 4A shows a bilateral embodiment of a dynamic interspinous implant device 10 according to the present invention. This embodiment differs from the unilateral embodiment of FIG. 3A in that the top jaw 18' of the top clamping mechanism 16 and the bottom jaw 18' of the bottom clamping mechanism 16 extend further than the corresponding jaws 18 in the embodiment of FIG. 3A. The intermediate jaws 18 are the same. Jaws 18' extend sufficiently to further connect with a second shaft 14 that is mounted on a side of the spinous processes 8 that is opposite the side of the spinous processes that the first shaft 14 is mounted on, and will be described in more detail below. Thus, jaws 18' each have an additional threaded boss 22 at a distal end portion thereof, in addition to the threaded boss 22 provided at the proximal end portion thereof. These bosses 22 are of the same construction described above, and thus are configured to receive the second shaft 14. Threaded nuts 26 can then be threaded over the bosses 22 in the same manner as described above, to connect the second (distal) ends of the jaws 18' to the second shaft, either slidably, or fixedly, depending upon the amount of torque applied by the nuts 26 against the second shaft 14 and bosses 22/jaws 18'. This configuration allows flexion and extension of the vertebrae that are connected by device 10. FIG. 4B shows an exploded view of the device 10 of FIG. 4A, for increased clarity of visualization of the components.

Figure 5A:
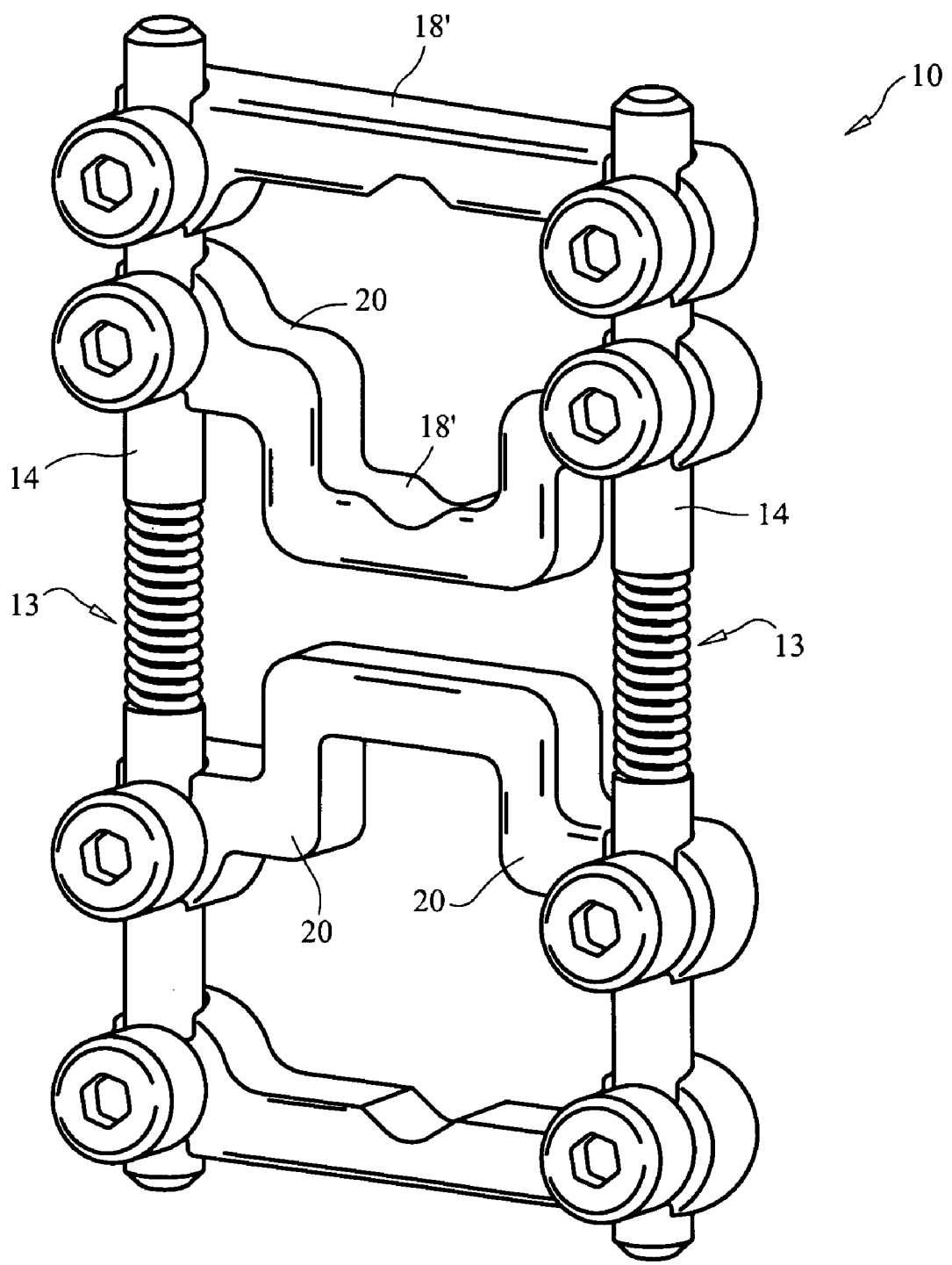
FIG. 5A shows another embodiment of a bilateral dynamic interspinous implant device according to the present invention.
Figure 5B:
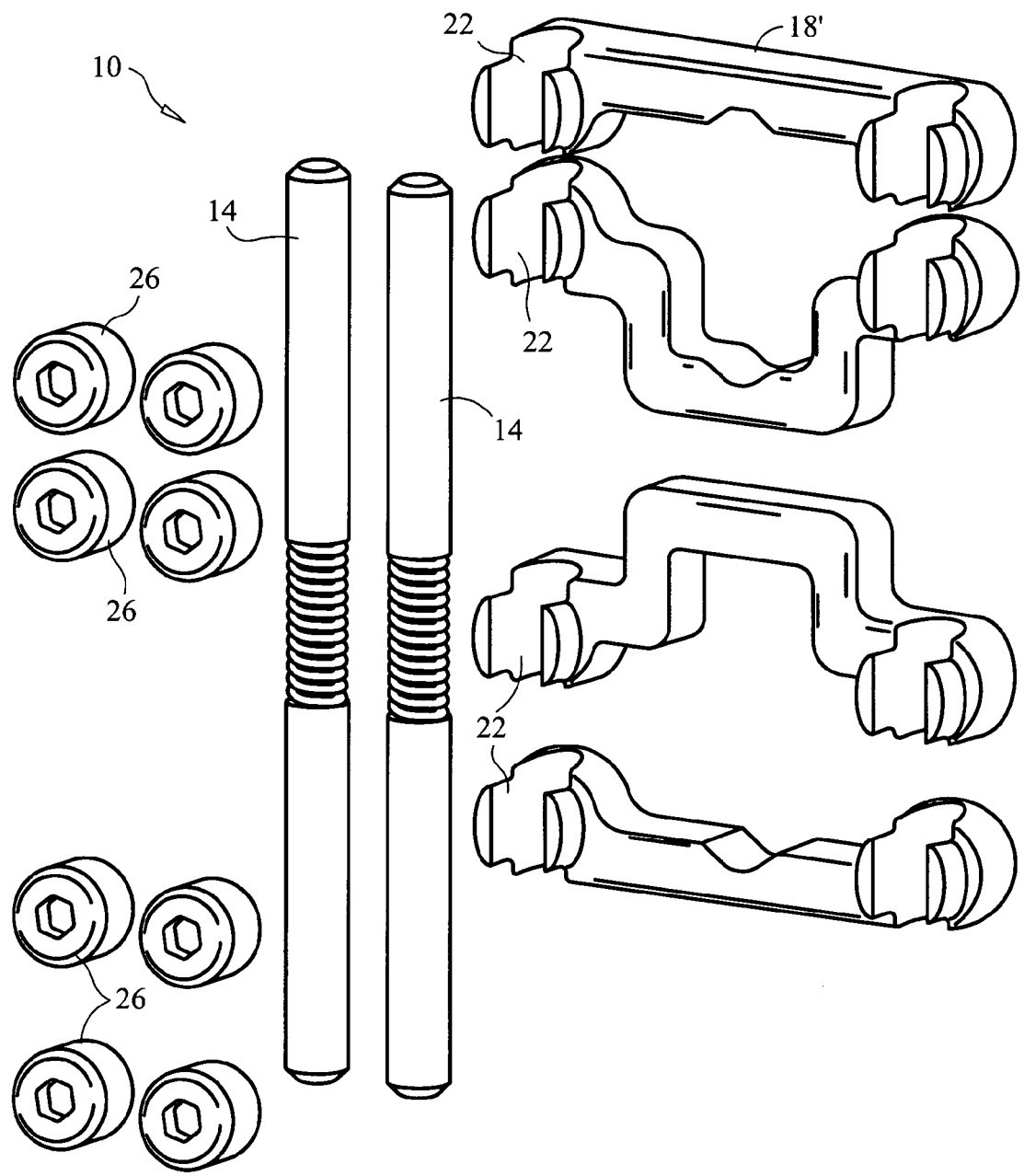
FIG. 5B shows an exploded view of the device of FIG. 5A.

FIG. 5A shows another bilateral embodiment of a dynamic interspinous implant device 10 according to the present invention. This embodiment differs from the bilateral embodiment of FIG. 4A in that the intermediate jaws 18' extend further than the intermediate jaws 18 of the embodiment of FIG. 4A and thus all jaws 18' extend further than the corresponding jaws 18 in the embodiment of FIG. 3A. Jaws 18' extend sufficiently to further connect with second shaft 14 that is mounted on a side of the spinous processes 8 that is opposite the side of the spinous processes that the first shaft 14 is mounted on, and, in this case second shaft 14 is mounted to both jaws 18' of both clamping mechanisms 16. Note that the intermediate jaws 18' may include dog-leg shaped portions at both end portion to move the attachment locations of the jaw pairs closer together on both shafts 14 thereby leaving greater space for the dynamic central portions 13 of the shafts 14. FIG. 5B shows an exploded view of the device 10 of FIG. 5A, for increased clarity of visualization of the components.

FIGS. 6A-6E show alternative embodiments of shaft 14 that may be employed singly in a unilateral embodiment of the present invention, or in pairs in a bilateral embodiment of the present invention. In FIG. 6A slots 13s are cut into the dynamic portion 13 of shaft 14 to make it more susceptible to bending as compared to the solid portions of the shaft. Although not limited to this configuration, the slots 13s in FIG. 6A comprise two sets of "Z" shaped slots, rotated at 90 degrees. The slots 13s collapse upon one another to limit the amount that the shaft 14 can bend. When used in a unilateral configuration, the shaft of FIG. 6A provides dynamics for lateral bending, flexion and extension, but not axial rotation. When a pair of the shafts 14 of FIG. 6A are used in a bilateral device 10, they provide dynamics for flexion and extension, but not lateral bending or axial rotation.

In FIG. 6B, two sets of profile slots 13A and 13B are cut into the shaft 14, rotated at 90 degrees. The collapse of the gaps 13A and 13B control how much the shaft 14 can bend. Thus different gap widths can be provided to vary the amount of bending allowed and thereby tailor the amount of bending allowed to the patient anatomy requirements. When used in a unilateral configuration, the shaft of FIG. 6B provides dynamics for lateral bending, flexion and extension, but not axial rotation. When a pair of the shafts 14 of FIG. 6B are used in a bilateral device 10, they provide dynamics for flexion and extension, but not lateral bending or axial rotation.

In FIG. 6C, the dynamic portion 13 has a cross-sectional diameter that is less than the cross-sectional diameter of the end portions. This reduced cross-sectional portion 13 can be produced, for example, by "necking down" the shaft by a drawing process, for example, or may alternately be machined as such. When used in a unilateral configuration, the shaft of FIG. 6C provides dynamics for lateral bending, flexion and extension, but not axial rotation. When a pair of the shafts 14 of FIG. 6C are used in a bilateral device 10, they provide dynamics for flexion and extension, but not lateral bending or axial rotation.

In FIG. 6D, the proximal and distal shaft portions 14 are connected intermediately by a coil spring portion 13, which can be metallic or polymeric. When used in a unilateral configuration, the shaft of FIG. 6D provides dynamics for lateral bending, flexion, extension and axial rotation. When a pair of the shafts 14 of FIG. 6D are used in a bilateral device 10, they provide dynamics for flexion, extension, lateral bending and axial rotation.

In FIG. 6E, the dynamic portion 13 of shaft 14 comprises a deformable structure of resiliently compliant struts. When struts 13*t* deform, they do not cause pinch points. When used in a unilateral configuration, the shaft of FIG. 6E provides dynamics for lateral bending, flexion, extension and axial rotation. When a pair of the shafts 14 of FIG. 6E are used in a bilateral device 10, they provide dynamics for flexion, extension, lateral bending and axial rotation.

It is noted here that the dynamic shaft configurations of the present invention are not limited to those specific embodiments shown in FIGS. 6A-6E, but may vary. Other examples of dynamic portions 13 that may be used in shaft 14 include, but are not limited to, an assembly including elastic compressible members, Bellevue springs and a force fit member; dashpots, or other elastic, viscoelastic and/or otherwise compliant configurations.

Figure 7A:
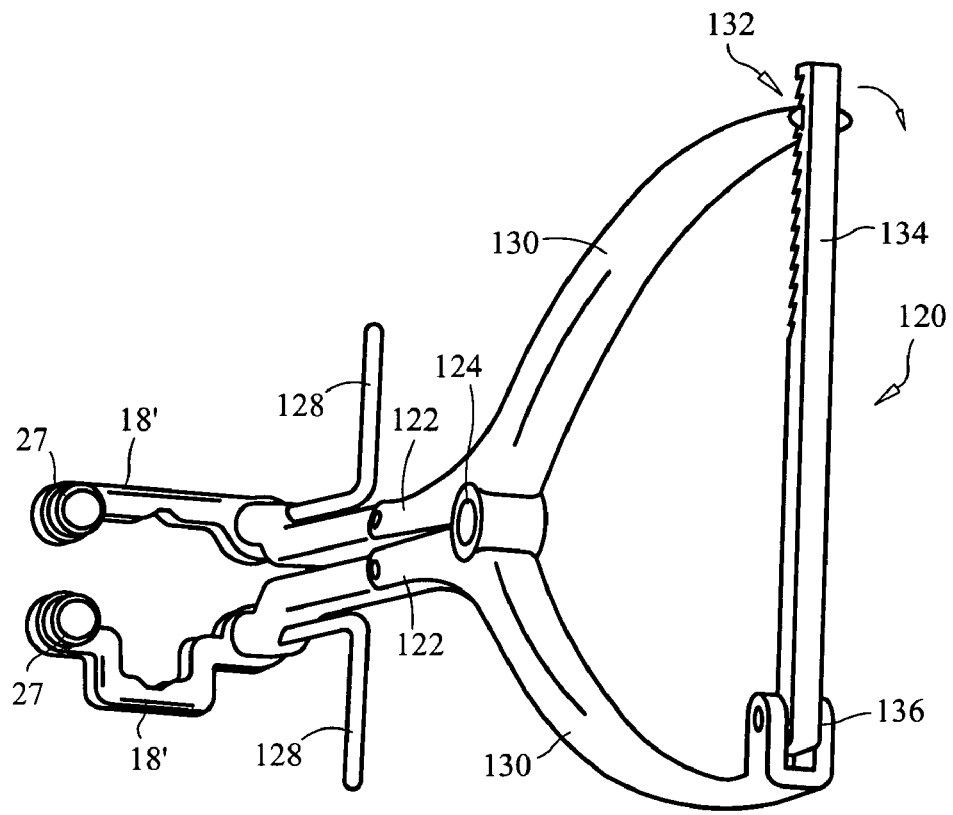
FIGS. 7A-7D show various views of a insertion tool and use thereof for attaching and inserting jaws.

FIG. 7A illustrates an insertion tool 120 with a pair of jaws 18' of a clamping mechanism 16 have been locked thereon in preparation for inserting the jaws through the interspinous ligament 11. Insertion tool 120 includes a pair of insertion arms 122 pivotally mounted at a pivot joint 124 and having rotatable engagement features 126 mounted at distal ends thereof as seen in the reverse view of FIG. 7B, and the enlarged, partial view of FIG. 7C. Each rotatable engagement feature 126 is configured to pass through a mating engagement feature 21 on one of the jaws 18' (or 18). As shown, engagement feature 126 is an oval-shaped protrusion and mating engagement feature 21 is an oval-shaped aperture. However, engagement features 126, 21 are not limited to this shape as many other shapes can be substituted, as long as the protrusion 126 can pass through the matching aperture 21 when in an unlocked state, and then, after rotating the protrusion by a predetermined amount (such as 90 degrees or some other predetermined amount of rotation), the protrusion 126 is prevented from passing back through the aperture 21.

Figure 7B:
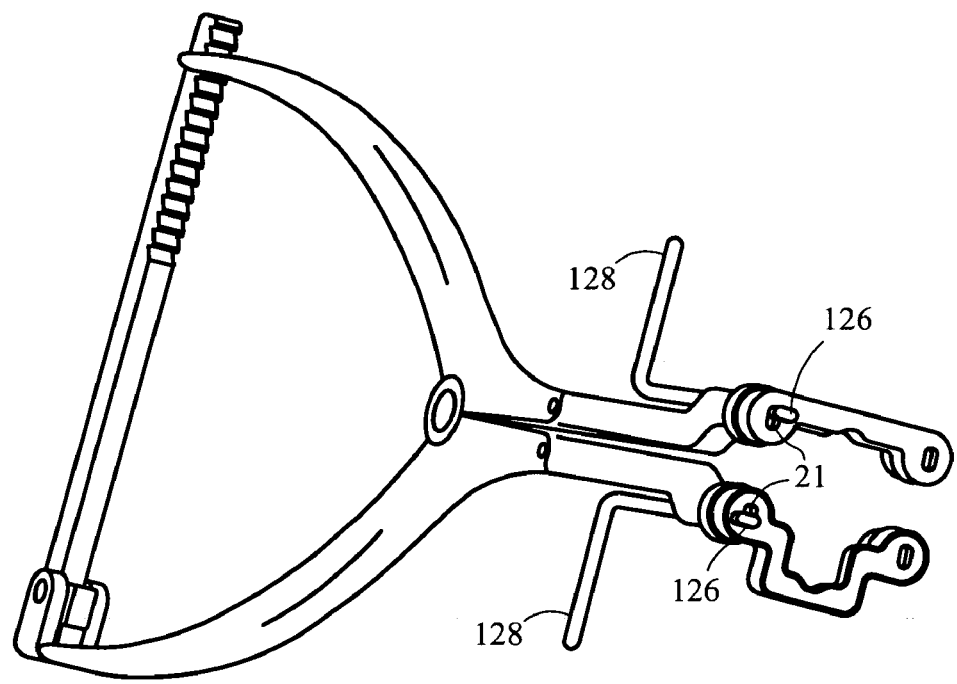
Figure 7C:
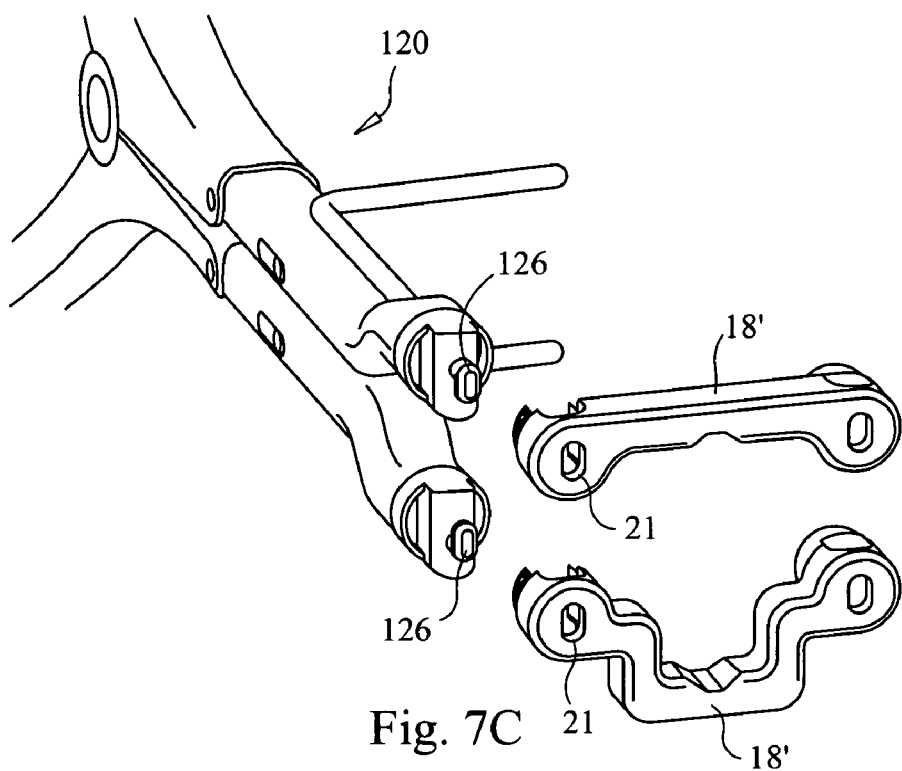

FIG. 7B illustrates the protrusions in the locked configuration, where it can be observed that the protrusions are not able to pass back through the apertures 21. FIG. 7C shows the protrusions 126 in the unlocked configuration, where the protrusions can pass through the apertures to either mount or dismount the jaws 18'. Locking arms 128 are connected to the protrusions 126 and are actuatable, by rotation thereof, to rotate the protrusions to either the locked or unlocked positions.

A pair of drive arms 130 are provided at a proximal end portion of tool 120 and are connected via pivot 124 to operate insertion arms 122. Drive arms are operable to drive the insertion arms away from each other by squeezing together drive arms 130 or to drive insertion arms toward each other by moving the drive arms 130 away from one another. A lock mechanism 132 may be provided to maintain the insertion arms 122 and thus the jaws 18' mounted thereto apart by a desired distance determined by the distance between drive arms 130. For example, in FIG. 7A, the driving arm 132 shown at the top ratchets against a toothed rack 134 and is therefore held in position relative to the other driving arm 130 as it is advanced toward it. This facilitates maintaining the jaws 18', 18' at a desired separation distance so that they properly align with the locations of the interspinous ligament inferiorly and superiorly of the spinous process 8 where they are to be inserted.

After completion of the insertion of the jaws 18', or if the operator decides to reposition the arms 122 and thus the spacing between jaws 18', the operator can release the driving arms 130 to allow them to be moved apart by rotating rack arm 134 about pivot joint 136 in the direction indicated by the rotational arrow in FIG. 7A. After repositioning the driving arms as desired, rack arm 134 can be repositioned by counter-rotating it to again perform the locking function described.

Although shown with a pair of insertion arms, an insertion tool can alternatively be provided with only a single insertion arm so as to insert one jaw at a time, thus simplifying the tool 120 and the procedure. However, this also increases the operation time, and so is not necessarily the preferred embodiment of the tool.

Figure 7D:
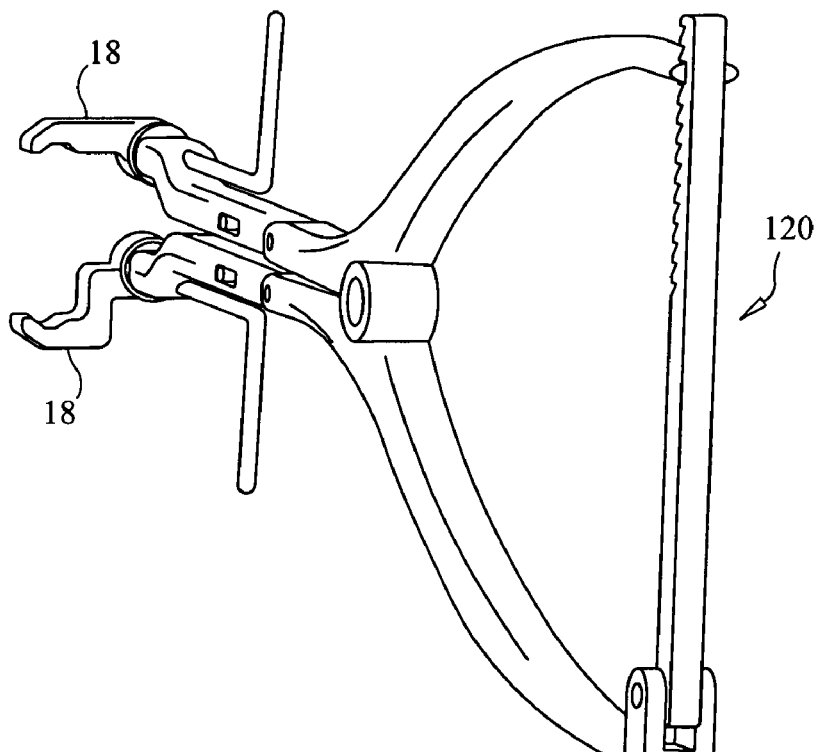

FIG. 7D illustrates insertion tool 120 having a pair of jaws 18 of a clamping mechanism 16 mounted thereto in preparation for placement/insertion of jaws 18 though the interspinous ligament 11 at the target locations. As shown, jaws 18 are attached and locked to, as well as manipulated by and released from tool 120 in the same manners as described above with reference to jaws 18'.

Referring now to FIGS. 8A-8H and 9A-9H, exemplary embodiments of implantation of a unilateral device 10 and a bilateral device 10 are described respectively. It should be noted here that the present invention is not limited to these methods of implantation, as they may vary. For example, one or more jaws 18 and/or 18' may be pre-connected to first shaft 14, either slidably or fixedly, prior to inserting such jaws. Jaws 18 and/or 18' that are not pre-connected would typically be inserted prior to insertion of pre-connected jaws 18 and/or 18'. Other variations in the procedures are also possible, as would be apparent to those of ordinary skill in the art.

Figure 8A:
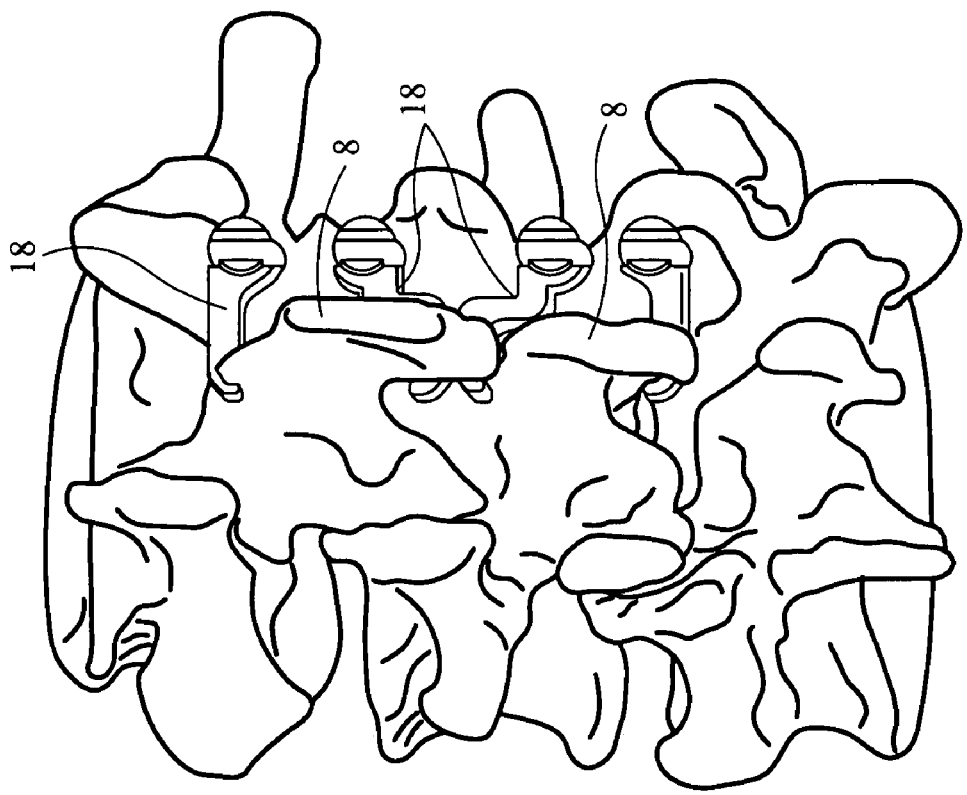
Figure 9B:
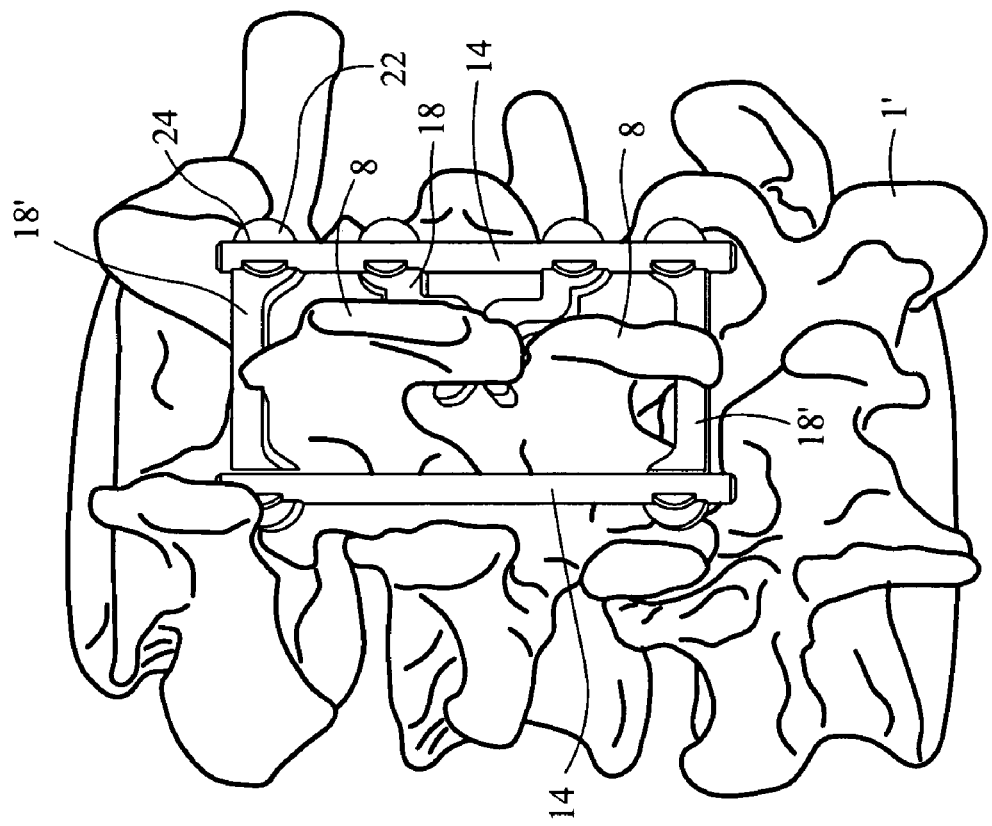
FIGS. 9A-9H illustrate an exemplary embodiment of implantation of a bilateral device according to the present invention.
Figure 9A:
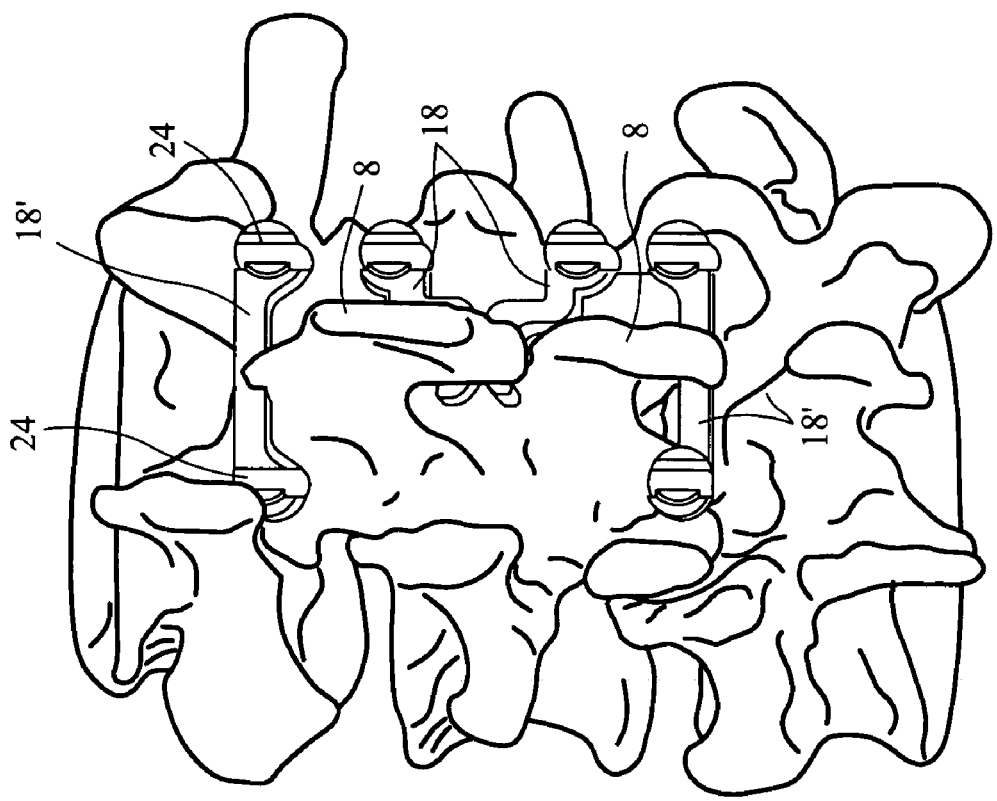

Device 10, whether unilateral or bilateral, single level or multi-level, can be implanted by a minimally invasive procedure. A small unilateral incision (e.g., in the range of about 20 mm to about 40 mm) is made to one side of midline (to the side of the line along which the spinous processes 8 lie) as an entry location for insertion. In the examples shown, the incision is made to the right of the midline, but, alternatively, the incision could be made to the left of the midline. The soft tissues are next gently stripped, such as with the use of a Cobb elevator or similar instrument. Using insertion tool 120, jaws 18 and/or 18' are next inserted through the interspinous ligament 11 at the target locations inferior and superior of the spinous processes 8 to be clamped, as illustrated in FIGS. 8A and 9A.

Figure 8B:
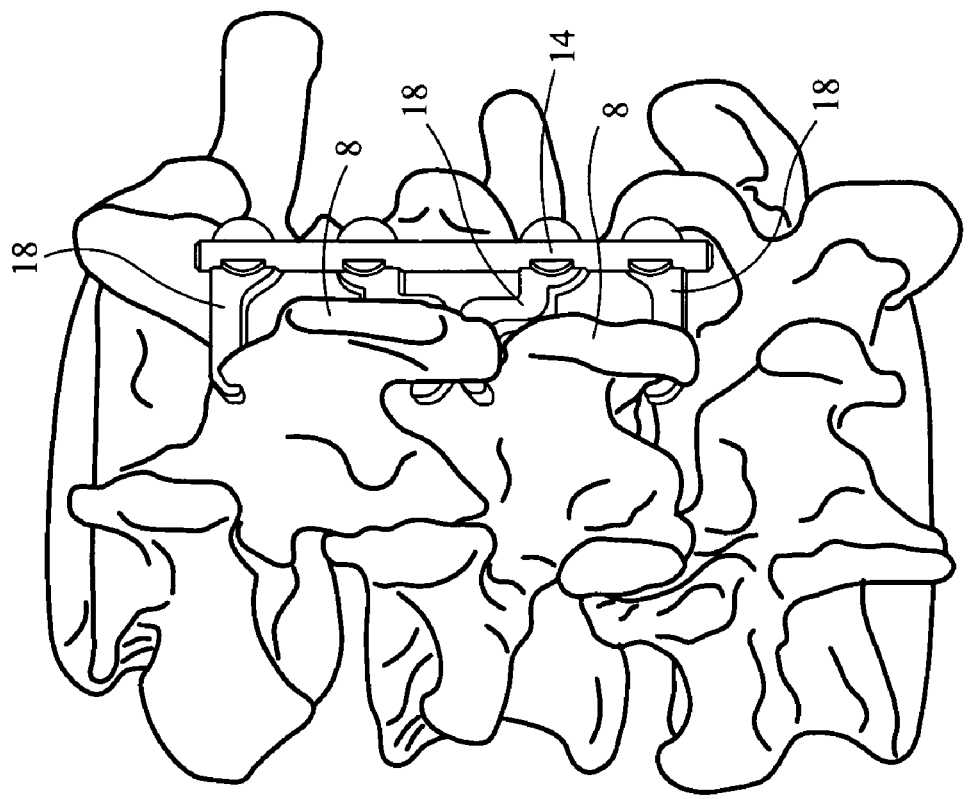
FIGS. 8A-8H illustrate an exemplary embodiment of implantation of a unilateral device according to the present invention.

FIG. 8B illustrates that after insertion and placement of jaws 18, shaft 14 is inserted into recesses 24 of the bosses 22 extending from the jaws. For a bilateral procedure, second shaft 14 is also inserted into the recesses 20 of the distal end portion bosses of any jaws 18' that are being used in the procedure, an example of which is illustrated in FIG. 9B.

Figure 8C:
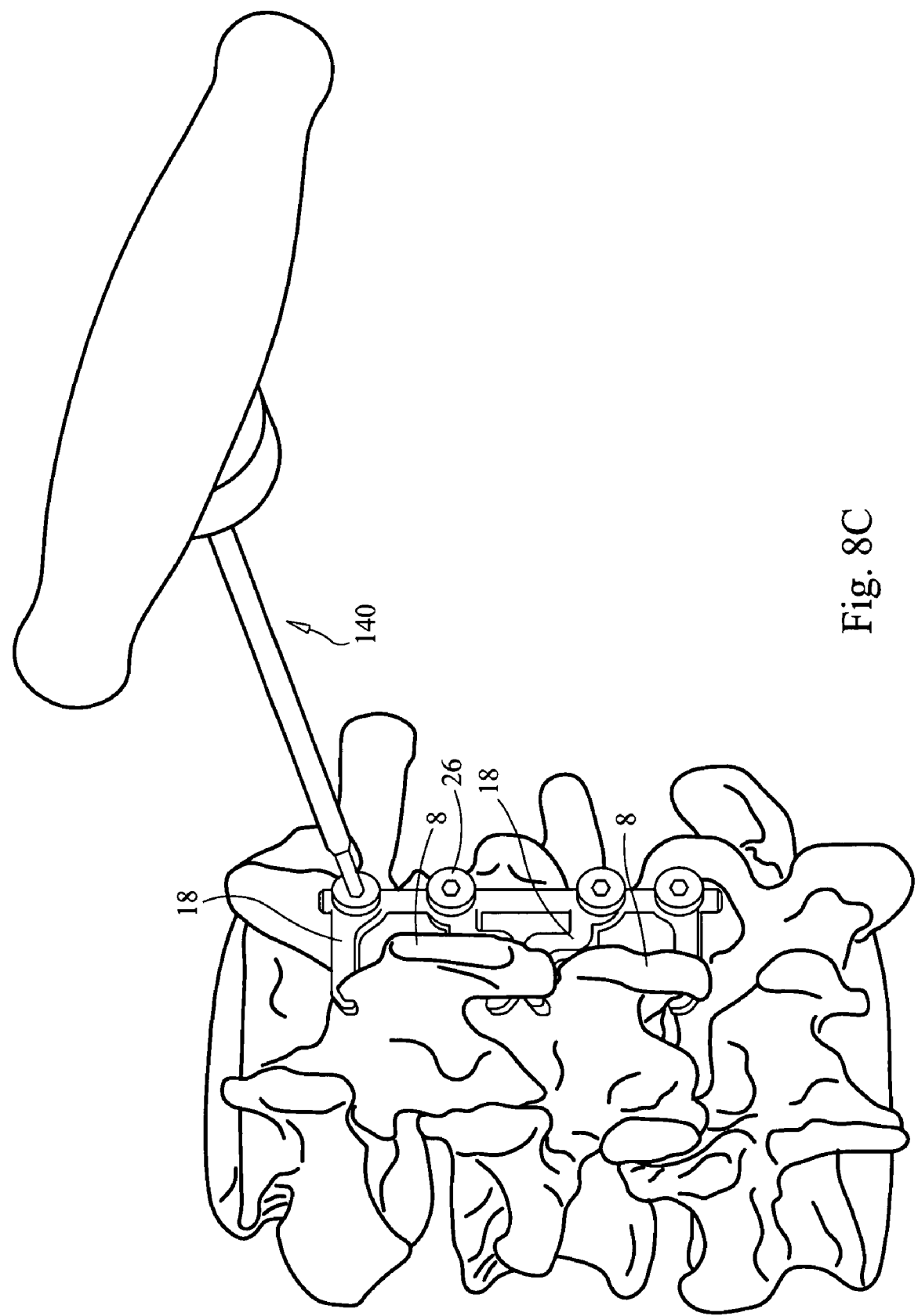
Figure 9C:
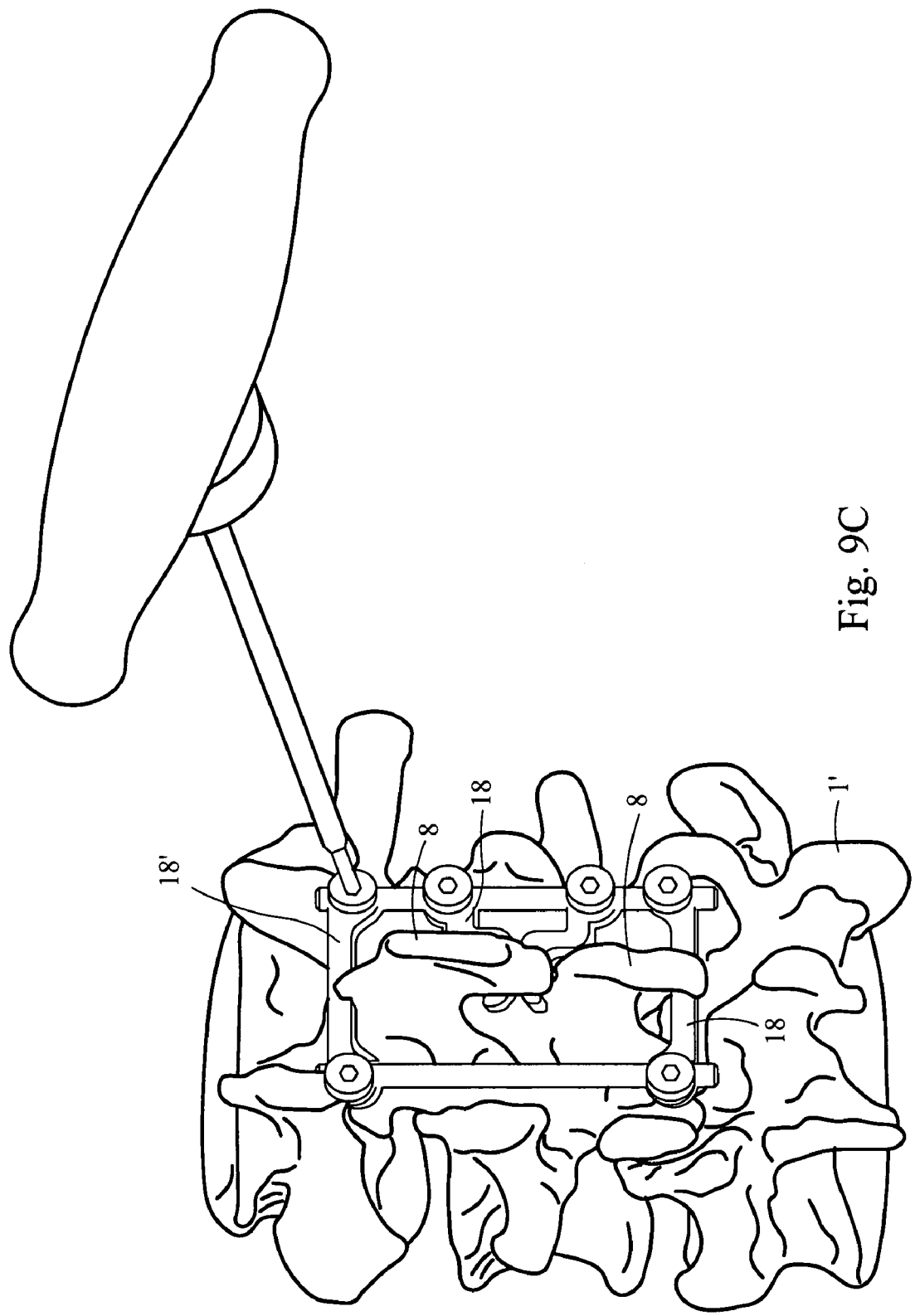

Next, threaded caps/nuts 26 are screwed onto threaded bosses 22, as illustrated in FIG. 8C. In the case of a bilateral procedure, such as shown in FIG. 9C or when four jaws 18' are used, protective caps 27, if used, are first removed from bosses 22 prior to screwing threaded caps/nuts over the bosses. A self retaining screwdriver 140 may be used to facilitate the installation of the threaded caps/nuts, as the distal end portion of screwdriver 140 retains a cap/nut 26 during delivery to the boss 22 and until cap/nut has been successfully threaded over the boss 22. At this time, threaded caps/nuts 26 are only loosely connected, to allow jaws 18 and/or 18' the ability to still slide relative to shaft(s) 14.

Figure 8D:
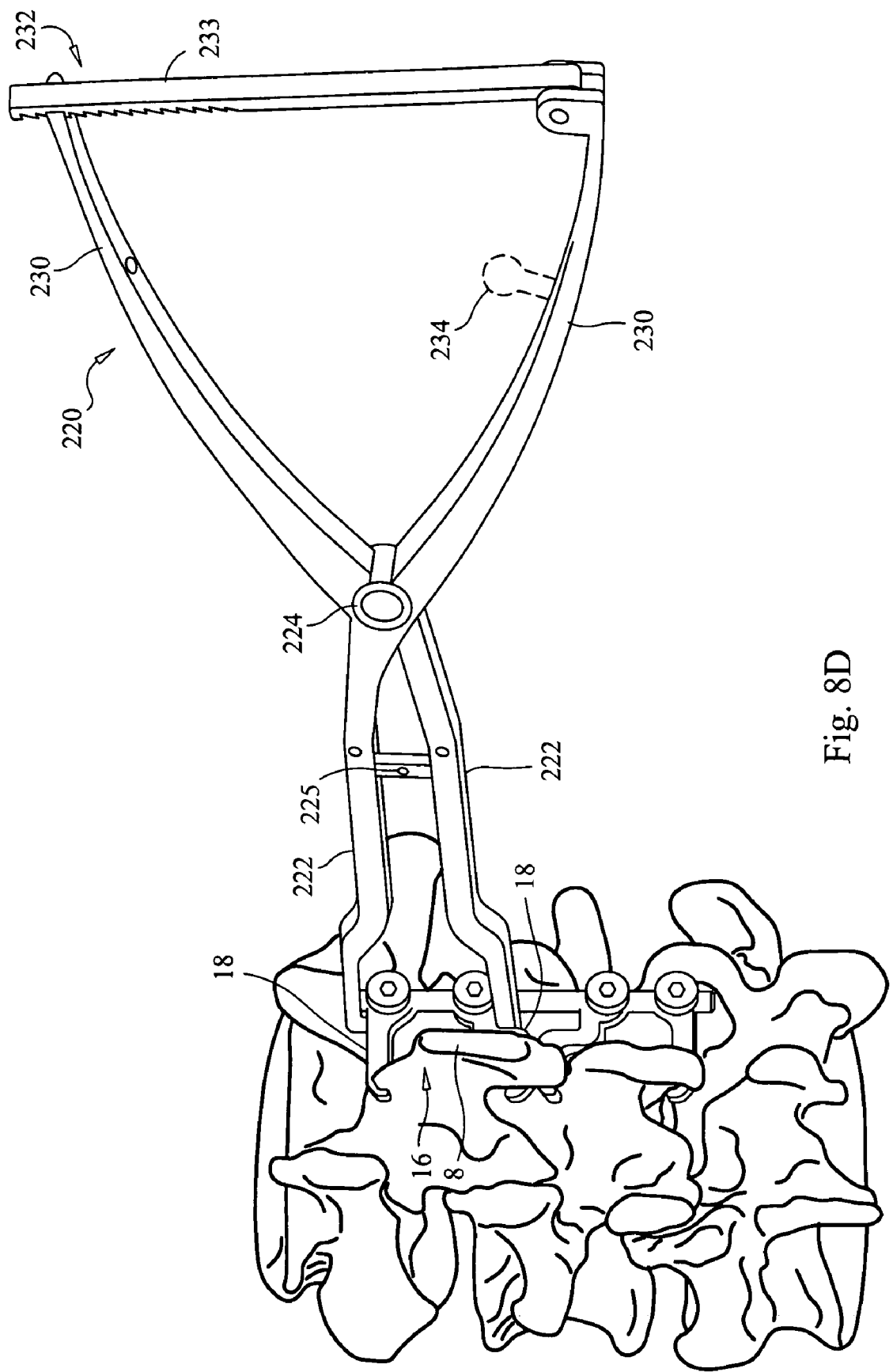
Figure 9D:
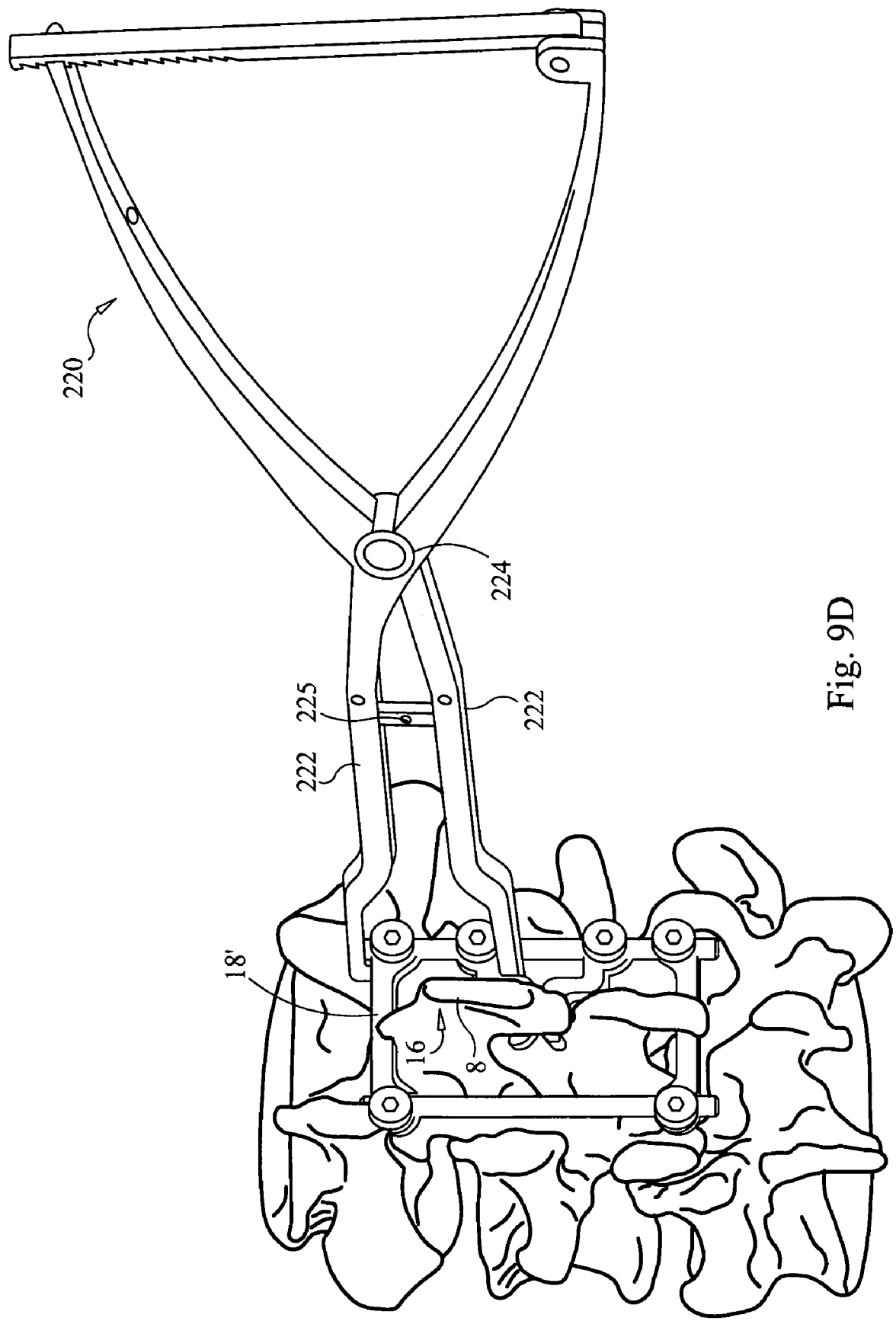
Figure 10A:
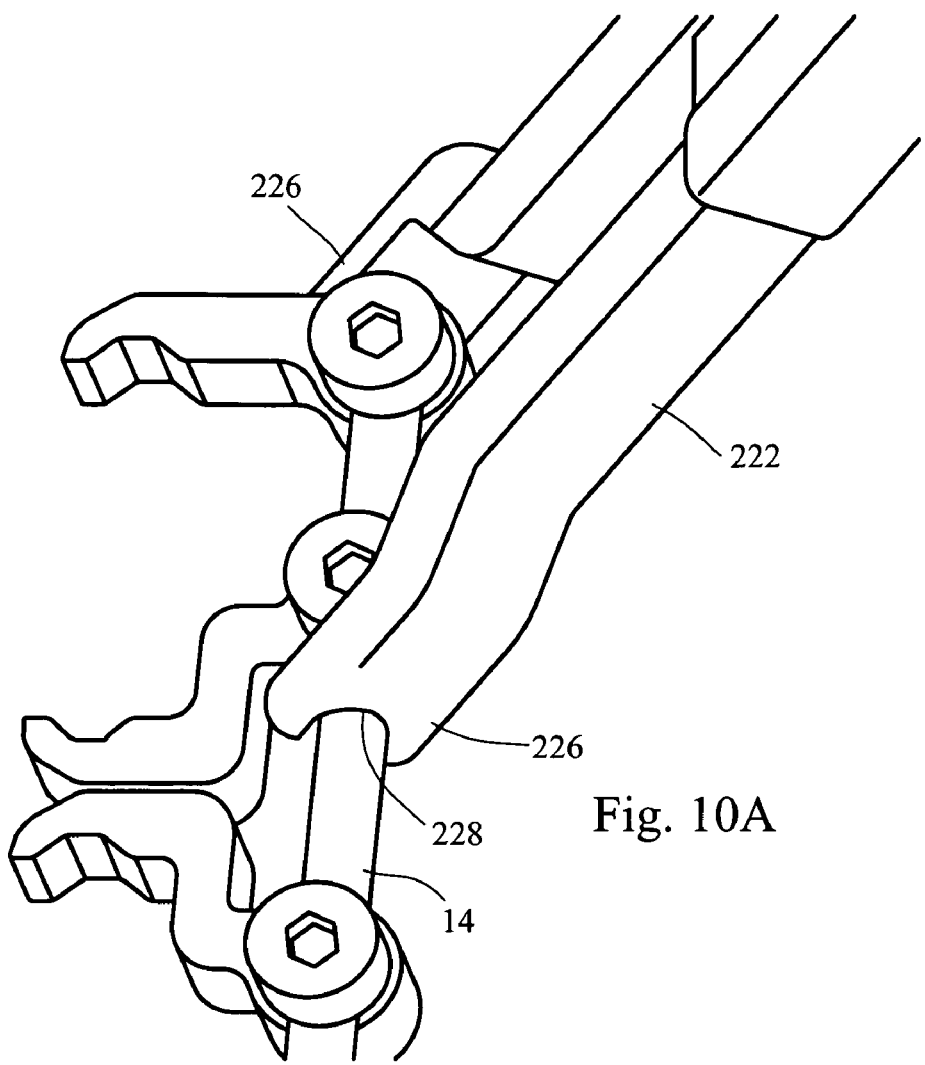
FIG. 10A is an enlarged, detail view showing use of the distal tips of a compression tool according to the present invention.

The superior clamping mechanism 16 is next clamped to superior and inferior surfaces of the spinous process 8 as illustrated in FIGS. 8D and 9D. A compression tool 220 may be used to compress the jaws 18 and/or 18' of clamping mechanism 16 in a manner illustrated in FIGS. 8D and 9D. Compression tool 220 includes a pair of compression arms 222 pivotally mounted at a pivot joint 224 and having distal tips 226 formed with recesses 228 (FIG. 10A) configured and dimensioned to receive shaft 14 therein. In this manner, tips 226 are guided along shaft 14 as they are driven toward one another to slide jaws 18 and or 18' toward one another in compression to clamp against the spinous process 8. Two connectors 225 connect compression arms 222 and connectors 225 pivot at first ends thereof 225a and slide at the other ends 225b (as shown in FIG. 10C) so that the arms 222 can move in parallel to one another during clamping, for example.

A pair of drive arms 230 are provided at a proximal end portion of tool 220 and are connected via pivot 224 to operate compression arms 222. Drive arms 222 are operable to drive the distal tips 226 of the compression arms 222 toward one another by squeezing together drive arms 230 or to drive compression arms apart from each other by moving the compression arms 230 away from one another. A lock mechanism 232 may be provided to maintain the compression arms 222 and thus the jaws 18 and/or 18' compressed thereby against spinous process by a desired distance or amount of compression. For example, in FIGS. 8D and 9D, the driving arm 230 shown at the top ratchets against a toothed rack 233 and is therefore held in position relative to the other driving arm 230 as it is advanced toward it. This facilitates maintaining the jaws 18 and/or 18' at a desired compression force against spinous process 8. This amount of compression can be maintained while the clamping mechanism 16 is locked against the spinous process to maintain the compression.

Optionally, a compression gauge 234 may be provided to indicate to the operator the amount of compression force that is being applied by the tips 226. For example, a strain gauge 236 (FIG. 10B) may optionally be provided on one or both tips 226 which can be wired to gauge 234 or wirelessly transmit data to gauge 234 to output the amount of compression that is being applied.

Figure 8E:
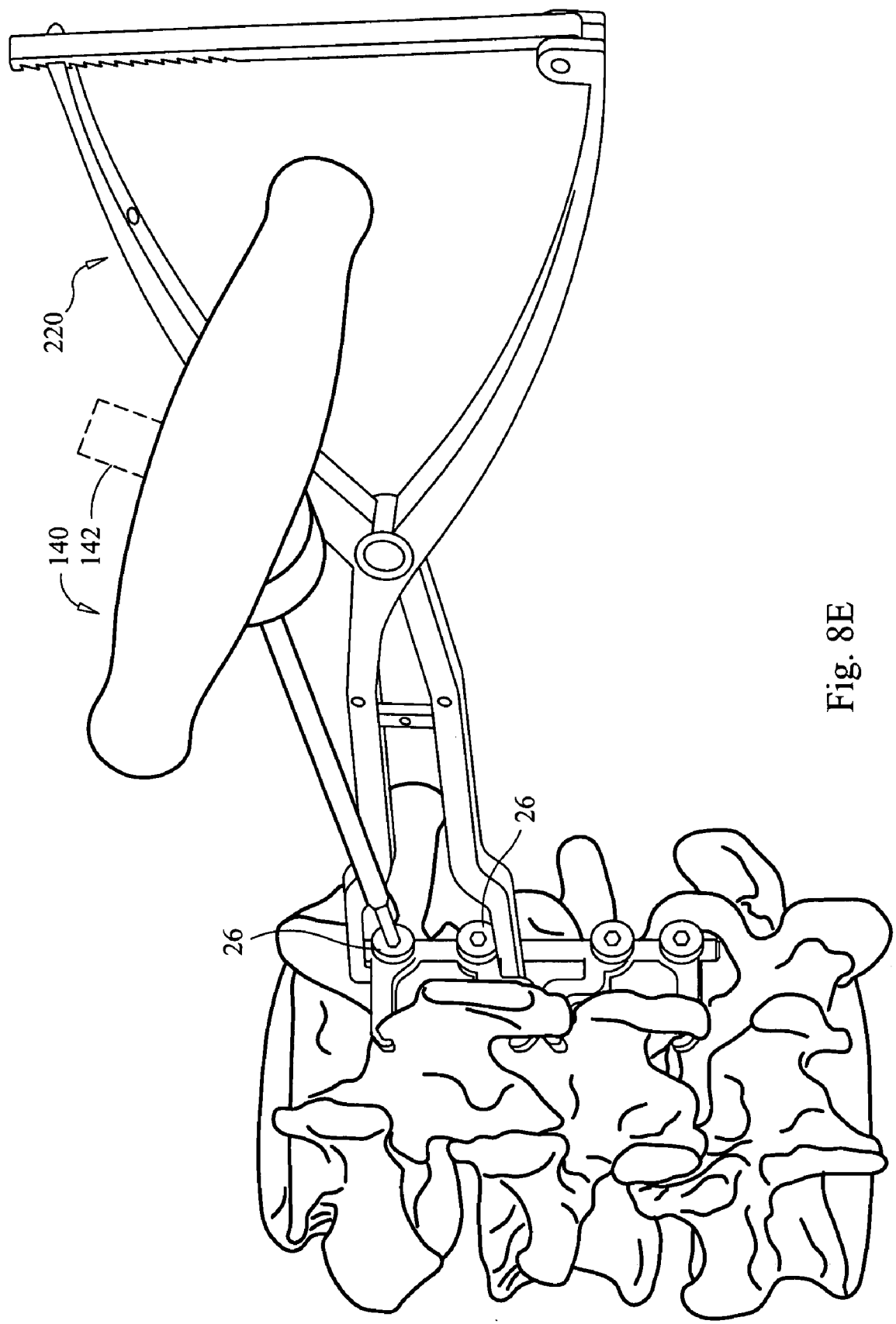
Figure 9E:
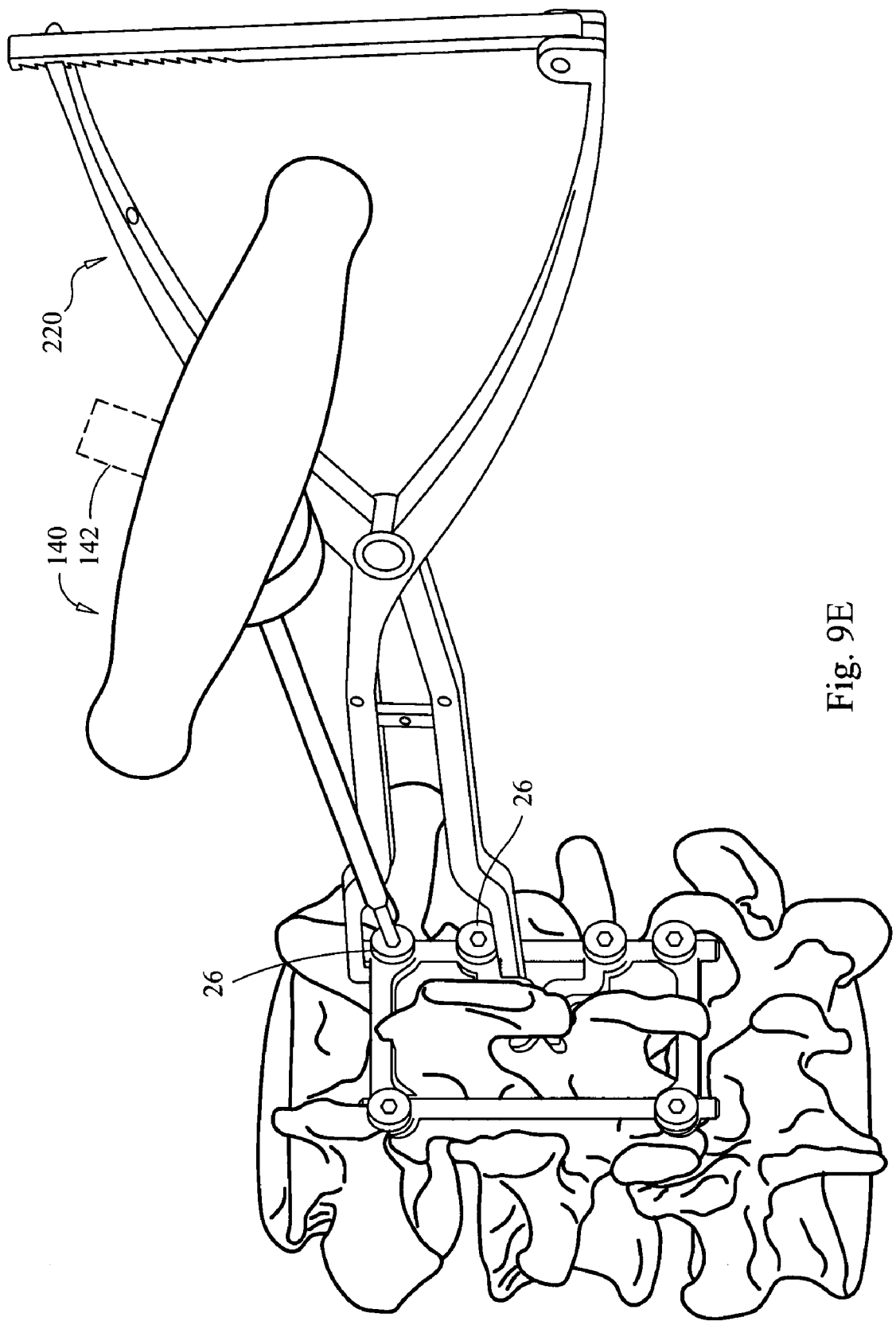

While maintaining the jaws 18 and/or 18' of the superior clamping mechanism under a desired amount of compression against the spinous process, all threaded caps/nuts 26 of the superior clamping mechanism 16 are torqued down to lock the jaws 18 and/or 18' relative to the one or two shafts 14, as illustrated in FIGS. 8E and 9E. Once the superior clamping mechanism has been locked, screwdriver 140 and compression tool are removed. Note that threaded caps/nuts may be torqued to a predetermined torque amount, as measured by a torque gauge 142 which may optionally be included on screwdriver 140

Figure 8F:
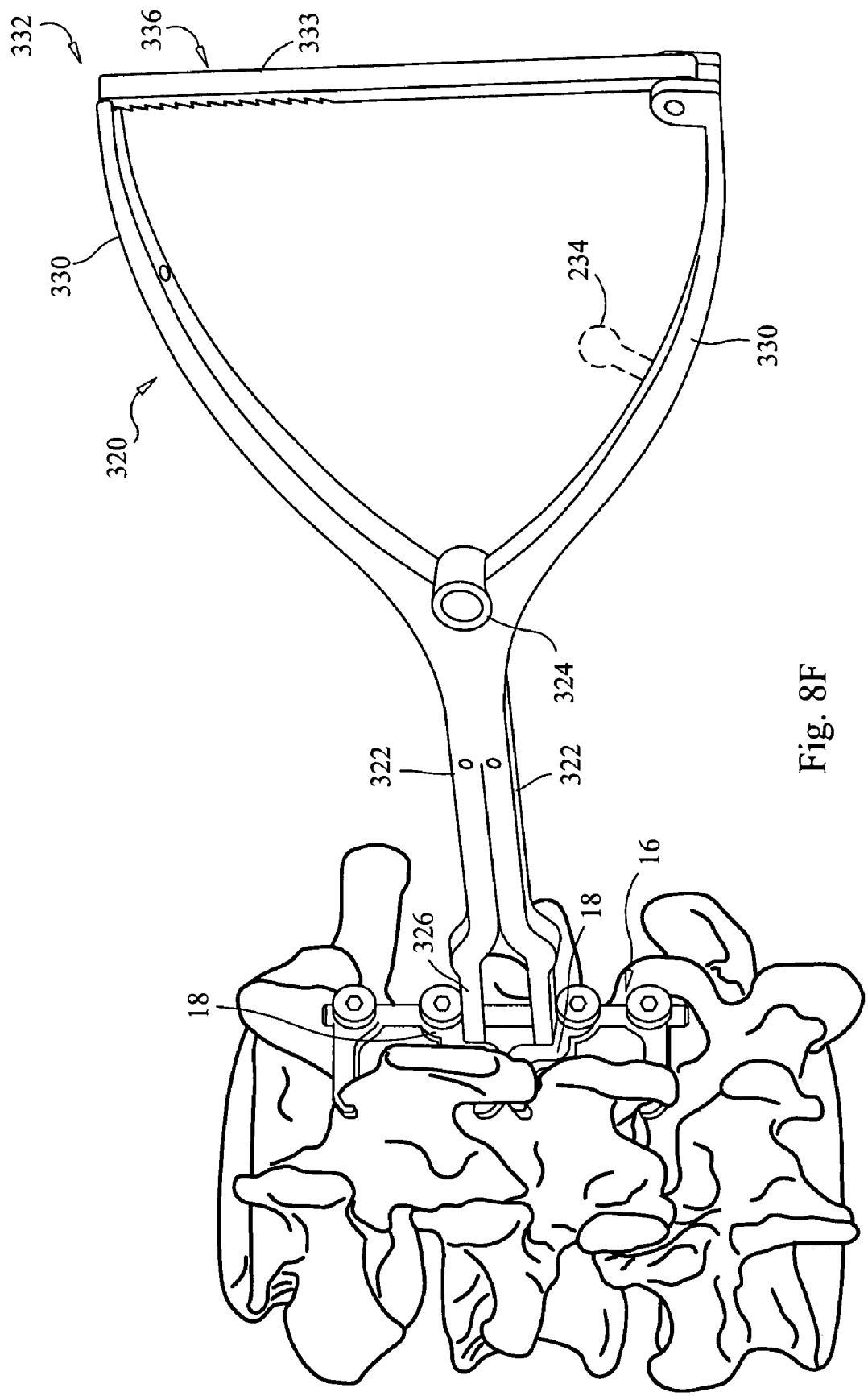
Figure 9F:
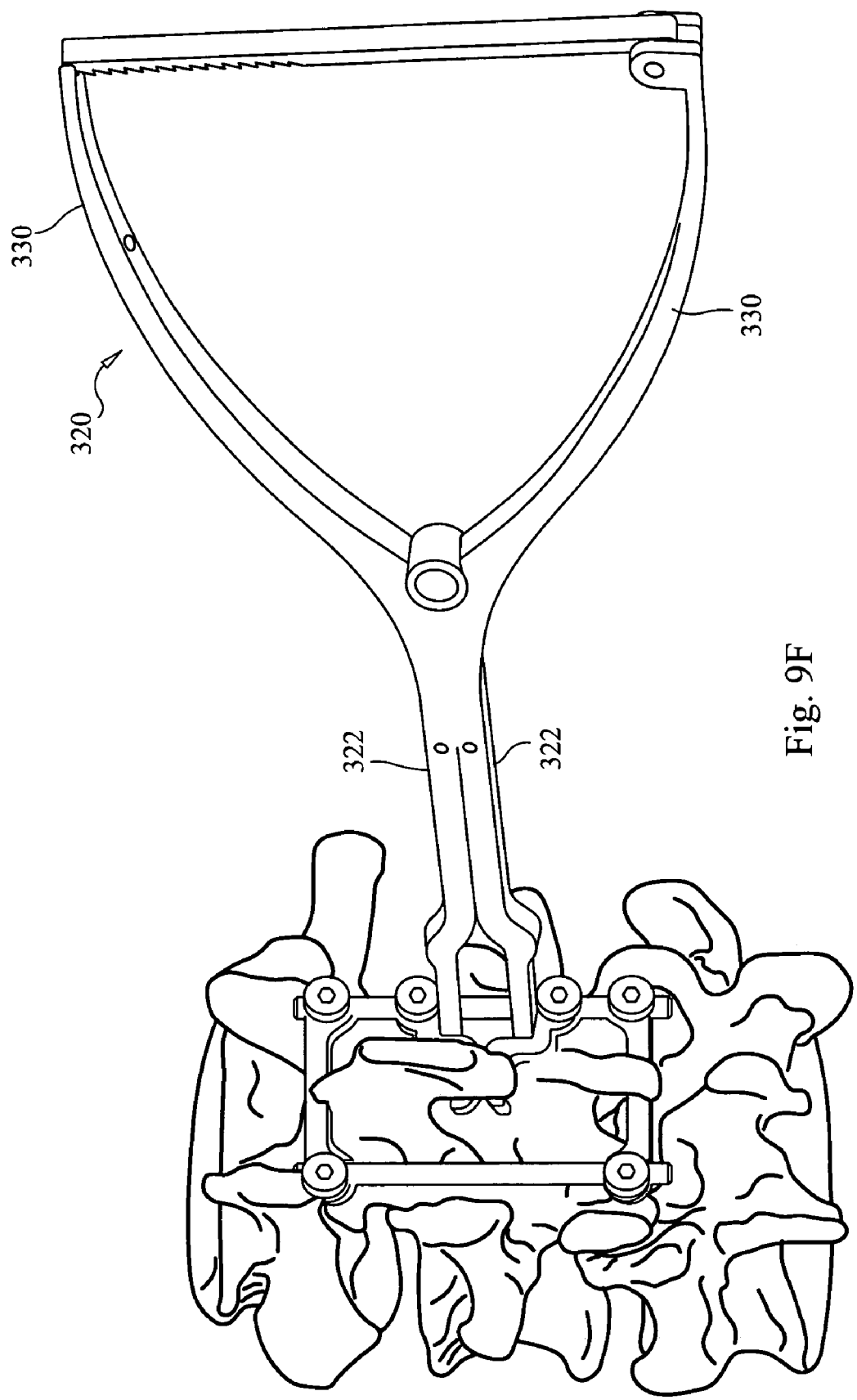

Next a desired amount of distraction between the superior and inferior spinous processes 8, 8 is performed as illustrated in FIGS. 8F and 9F. A distraction tool 320 may be used to accomplish this distraction. Distraction tool 320 is similar to compression tool 220 except that it is configured so that squeezing the drive arms together works through the pivot 324 to drive the distraction arms 322 apart from one another.

The distal tips 326 of distraction arms are provided with recesses like those of compression tool 220, which are configured and dimensioned to receive shaft 14 therein. In this manner, tips 226 are guided along shaft 14 as they are driven away from one another toward one another to slide the superior jaw 18 or 18' of the inferior clamping mechanism 16 away from the inferior jaw 18 or 18' of the superior clamping mechanism 16, as illustrated in FIGS. 8F and 9F.

Figure 8G:
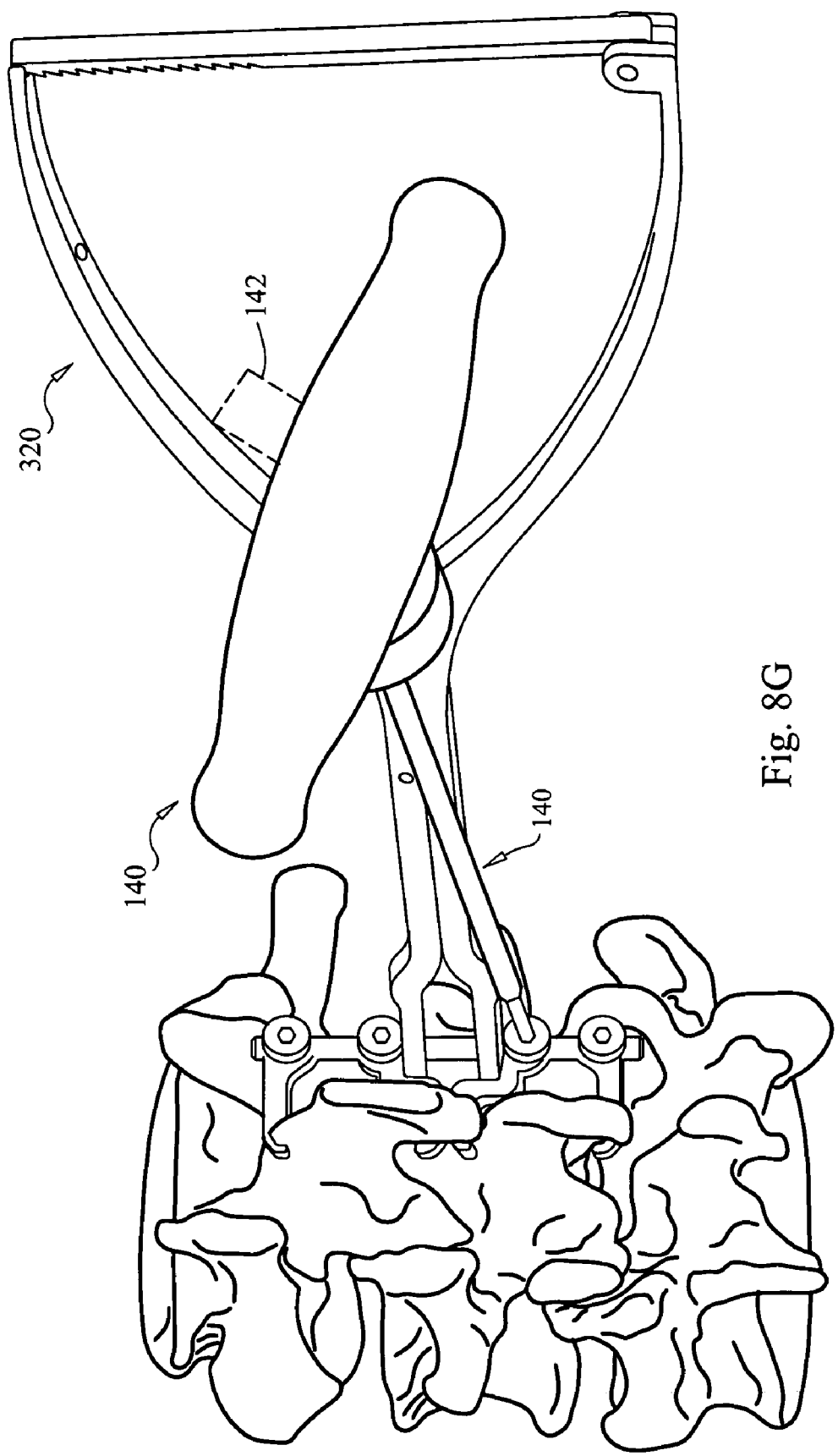
Figure 9G:
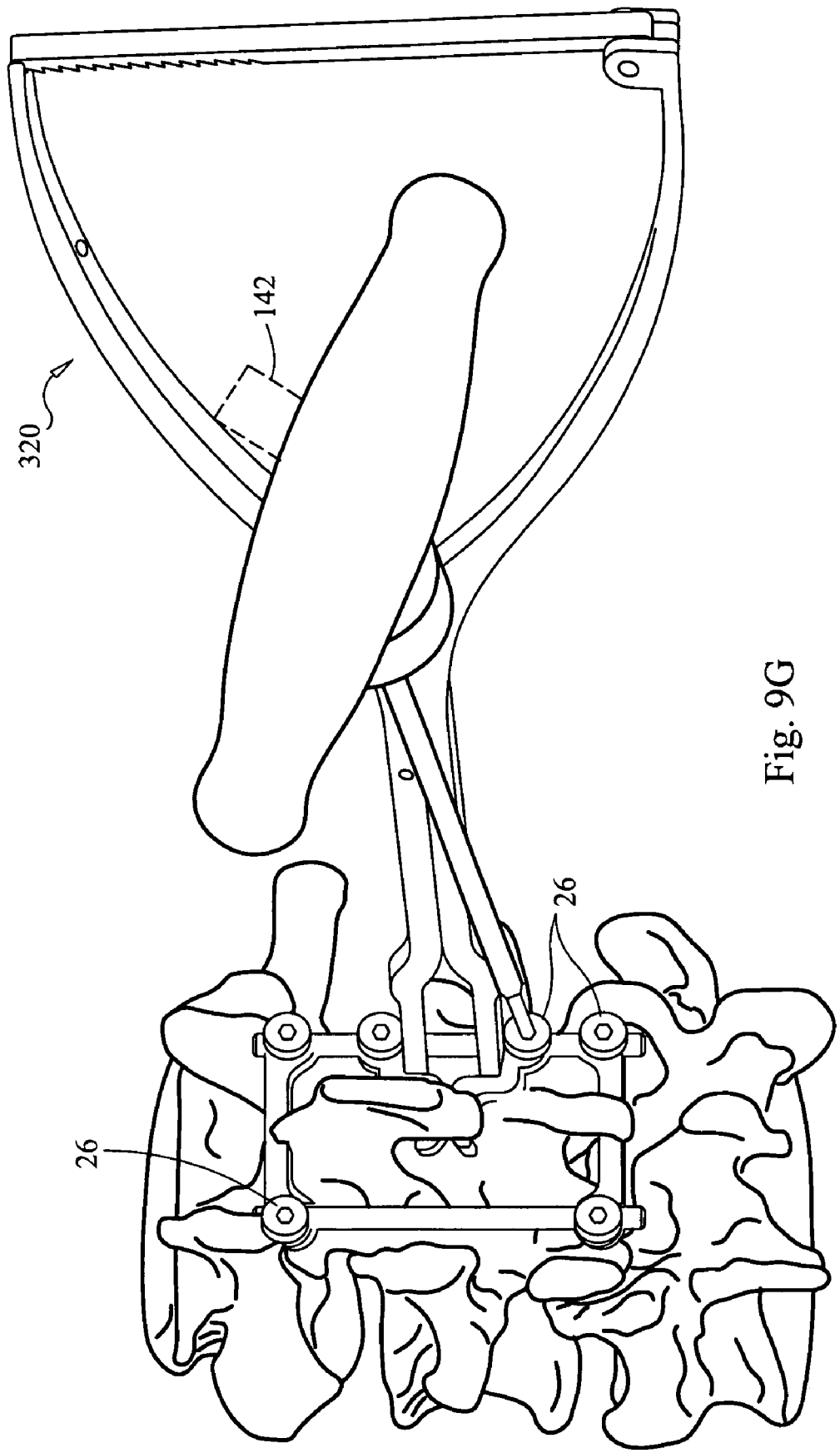

A lock mechanism 332 may be provided to maintain the distraction arms 322 and thus the jaws 18 and/or 18' distracted thereby by a desired distance or amount of distraction force. For example, in FIGS. 8F and 9F, the driving arm 330 shown at the top ratchets against a toothed rack 333 and is therefore held in position relative to the other driving arm 330 as it is advanced toward it. This facilitates maintaining the jaws 18 and/or 18' at a desired distraction distance or force against the jaws 18 and/or 18' and spinous processes 8, 8. This amount of distraction can be maintained while the superior jaw 18 or 18' of the inferior clamping mechanism 16 is locked against the one or two shafts 14 to maintain the distraction, as illustrated in FIGS. 8G and 9G.

Optionally, a force gauge 234 may be provided to indicate to the operator the amount of distraction force that is being applied by the tips 226. For example, a strain gauge like strain gauge 236 shown in FIG. 10B, may optionally be provided on one or both tips 326 which can be wired to gauge 234 or wirelessly transmit data to gauge 234 to output the amount of distraction force that is being applied. Additionally or alternatively, a scale 336 may be provided on toothed rack 333 to indicate the amount of distraction distance applied.

While maintaining the superior jaw 18 or 18' of the inferior clamping mechanism 16 at a desired amount of distraction distance or force relative to the inferior jaw 18 or 18' of the superior clamping mechanism, the threaded cap/nut 26 is torqued down to lock the superior jaw 18 or 18' relative to the one or two shafts that it is connected to. Alternatively, if micro-compression is called for rather than distraction, compression tool 220 is used at FIGS. 8F and 9F, rather than the distraction tool 320, and micro-compression is performed by driving the inferior jaw 18 or 18' of the inferior clamping mechanism 16 toward the inferior jaw 18 or 18' of the superior clamping mechanism 16 by a desired distance or compression force, by applying tips 226 to those jaws and operating compression tool 220 in a manner already described above. Then, at FIGS. 8G and 9G, while maintaining the desired amount of micro-compression, each threaded cap/nut 26 of the inferior jaw 18 or 18' of the inferior clamping mechanism is torqued down to lock this jaw relative to the one or two shafts that it is connected to, such as by using screwdriver 140 and, optionally, torque gauge 142.

In either case, the screwdriver and either the distraction tool 320 or the compression tool 220 are removed after locking down the superior jaw 18 or 18' of the inferior clamping mechanism 16 (in the case of distraction) or the inferior jaw 18 or 18' of the inferior clamping mechanism 16 (in the case of micro-compression).

Figure 8H:
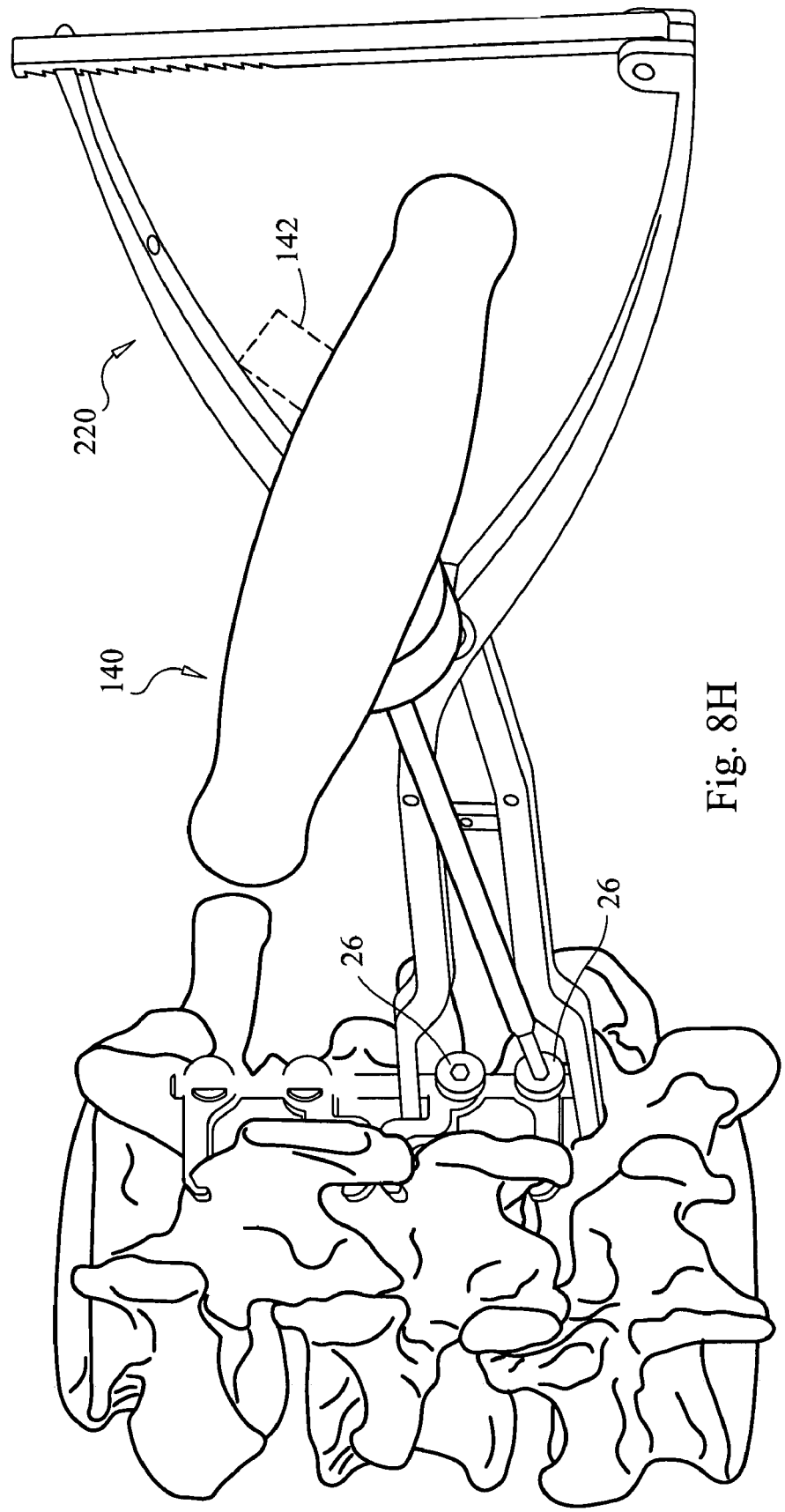
Figure 9H:
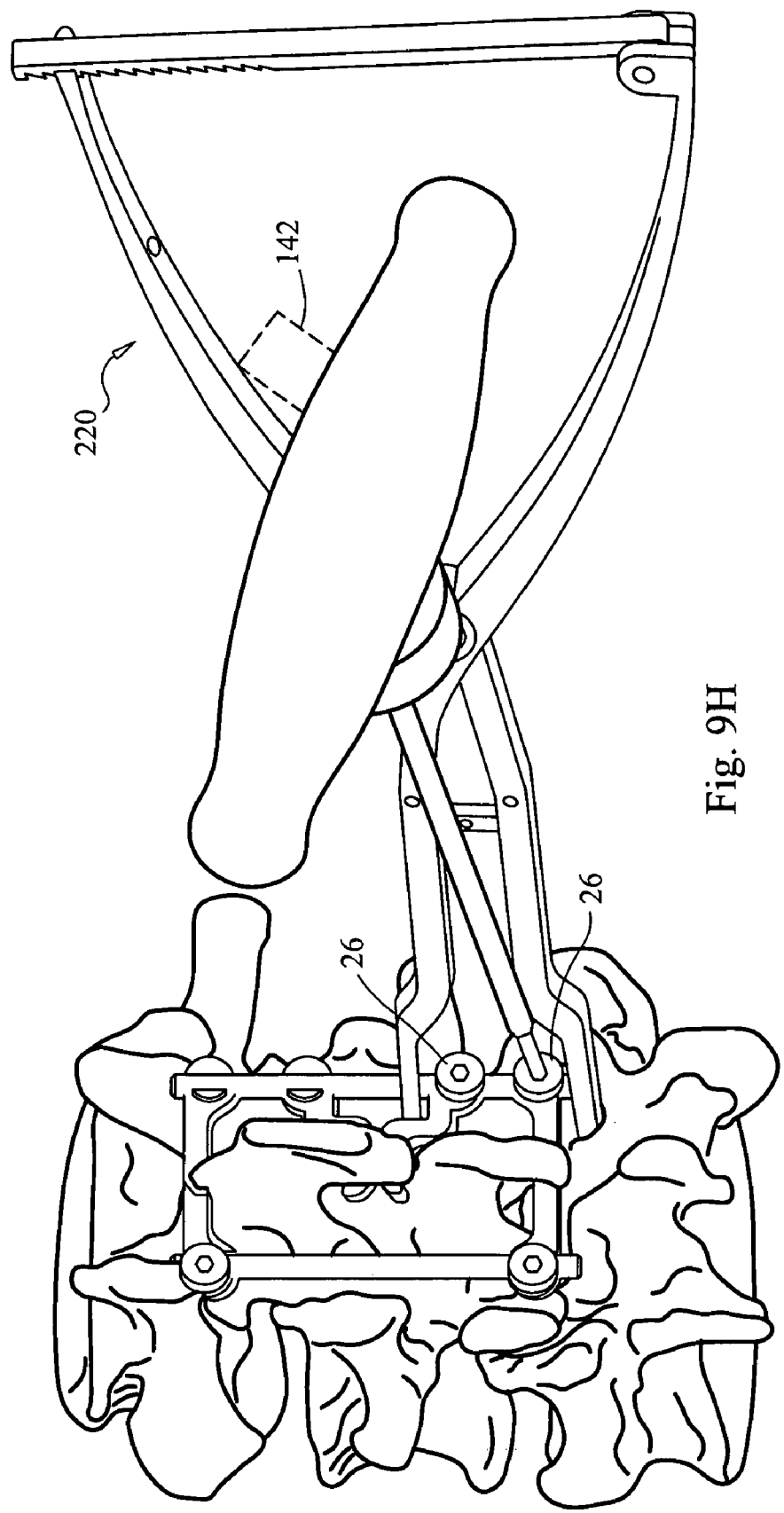

Next, at FIGS. 8H and 9H, the compression tool 220 is used to apply the distal tips to the jaws 18 and/or 18' of the inferior clamping mechanism so as to apply a desired amount of clamping force to the inferior spinous process 8 in a manner as described above with regard to the superior spinous process. In the case of distraction, the inferior jaw 18 or 18' of the inferior clamping mechanism 16 is then locked against the one or two shafts 14, as illustrated in FIGS. 8H and 9H. In the case of micro-compression, the superior jaw 18 or 18' of the inferior clamping mechanism 16 is then locked against the one or two shafts 14.

All tools are then removed, and the patient is closed up (including closing the small incision) to complete the procedure. At a later time, the site can be re-entered to adjust one or more distraction levels, if desired, using the same tools and procedures already described above.

Figure 11A:
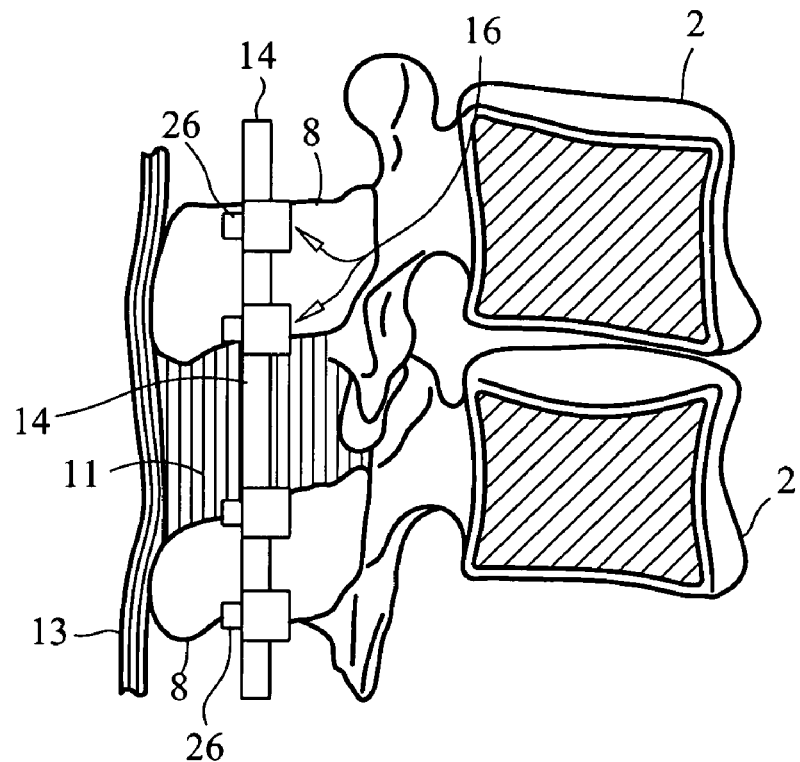
FIG. 11A is a side view of a device having been implanted according to an embodiment of the present invention.
Figure 11B:
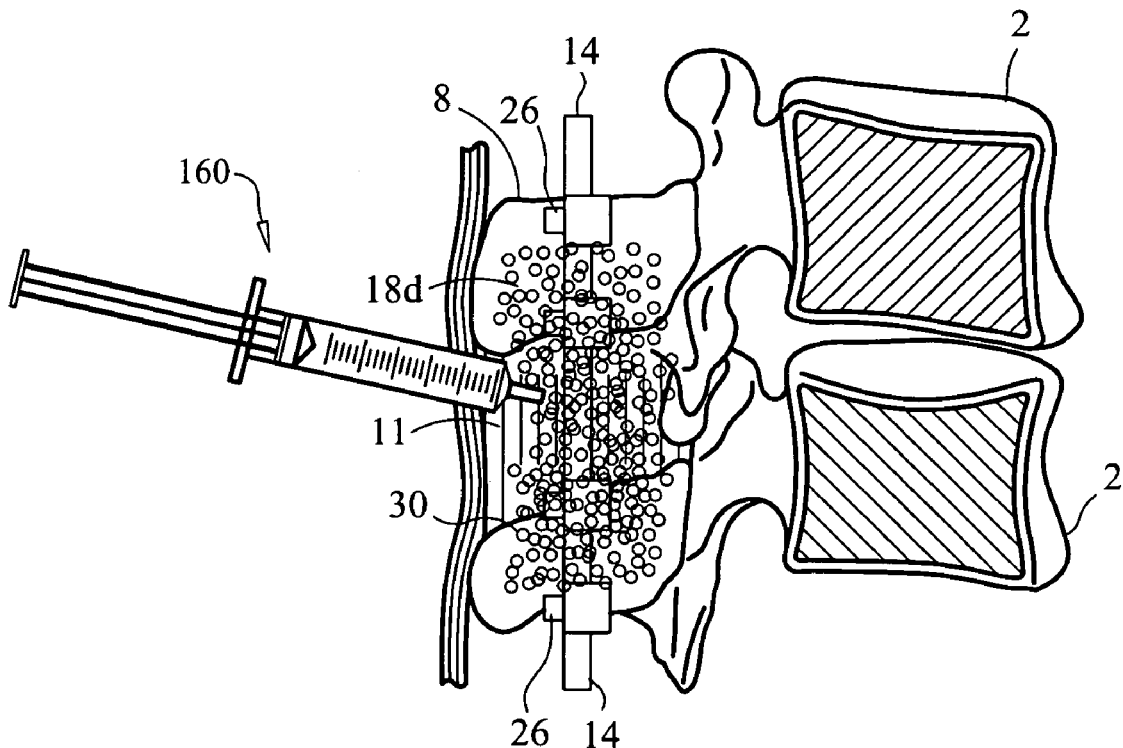
FIG. 11B illustrates implantation of a slurry of bone ingrowth material after implantation of the device in FIG. 11A.

As noted above, device 10 may be used in the performance of a fusion procedure. In this case, device 10 is implanted in any of the same manners described above. Once device 10 has been placed, distracted to the amount desired (or used to apply micro-compression in the amount desired) and locked to maintain the desired configuration as illustrated in the side view of FIG. 11A, any tools used to perform the implantation can be removed and portions of the lamina 7 and spinous processes 8 may optionally be decorticated, using a high speed burr, for example, to encourage bone growth/regeneration/healing process. A protein substance, such as bone morphogenetic protein (BMP) (FIG. 11B), and/or one or more bone grafts (either solid (FIG. 11C) or particulate (FIG. 11B) or other bone growth enhancing material or agent 30 is implanted into the surgical site to contact at least portions of both of the vertebrae 1 spanned by device 10. as well as lamina 7. Preferably, at least a portion of device 10 is also contacted by the bone graft 30 material. Portions or all of device 10 may be covered/encapsulated by the bone growth enhancing material 30, with material 30 also contacting and covering at least portions of the spinous processes 8 that are contacted by device 10 and/or laminae 7 of those same vertebrae 7. Upon closing up the patient, the soft tissues surrounding the bone growth enhancing material 30 maintains the material 30 in place to allow tissue ingrowth to proceed in the desired locations. When used for fusion procedures, the single shaft 14 of a unilateral device 14 may use a substantially rigid and not include dynamic central portion 13, but be substantially rigid 14 throughout. Alternatively, any of the same shafts 14 that include a dynamic central portion 13 as described above may be used. Likewise, when used for fusion procedures, each of the two single shafts 14 may be substantially rigid and not include dynamic central portion 13, but be substantially rigid 14 throughout, or, alternatively, shafts 14 may be used that each include a dynamic central portion 13.

Figure 10B:
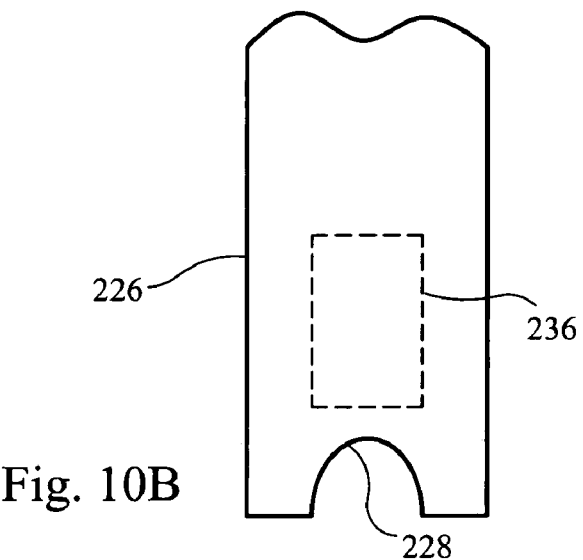
FIG. 10B is an enlarged, detail view showing an optional strain gauge on a distal tip.
Figure 10C:
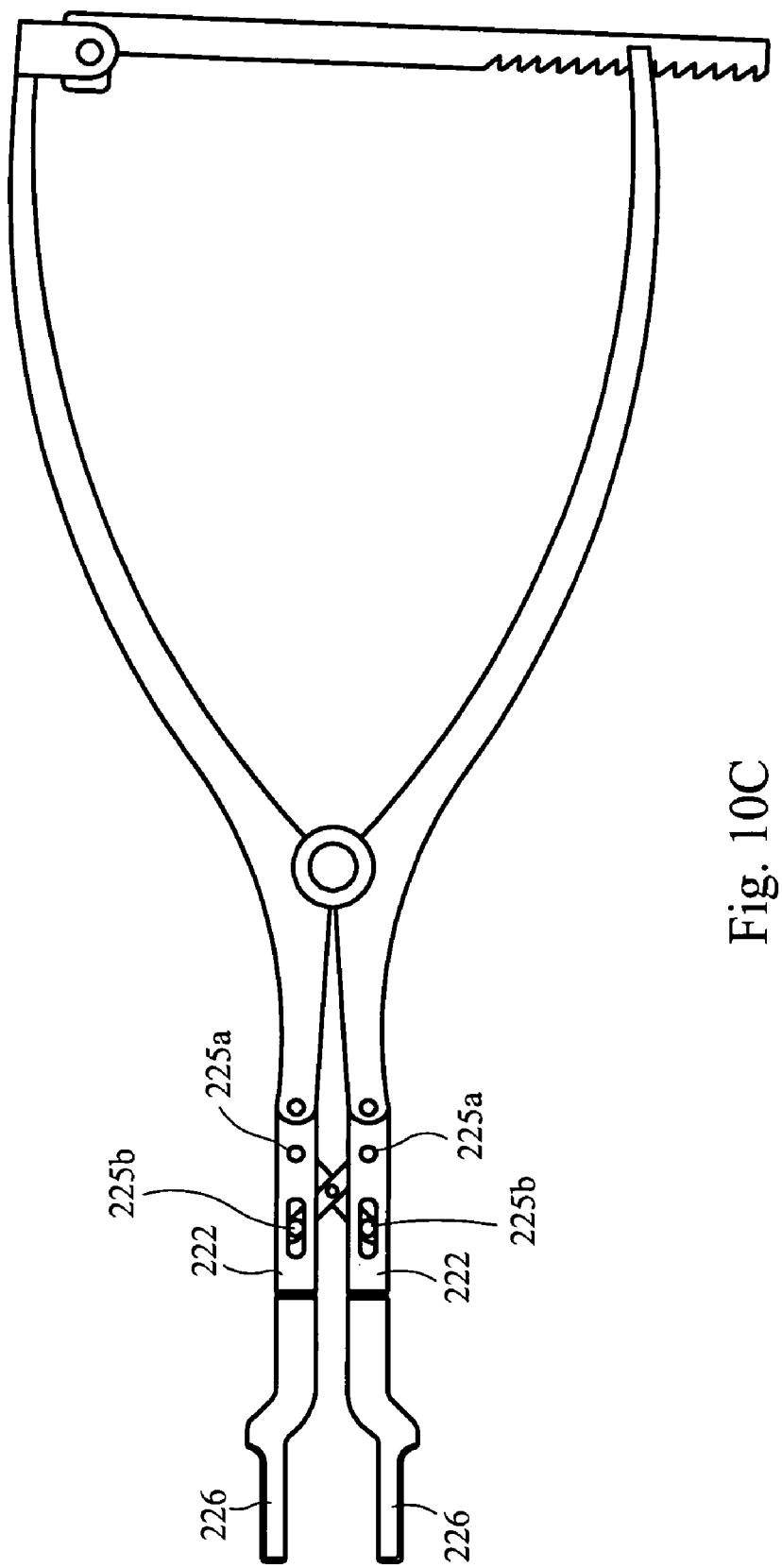
FIG. 10C is a plan view of a compression tool according to an embodiment of the present invention.

FIG. 10B illustrates implantation of a slurry of bone ingrowth material 30 after placement of device 10. In this case, the slurry is delivered via a delivery device 160 having a tube 162 that contains the slurry and a piston/plunger component 164 used to drive the material 30 out of the larger bore distal end of tube 162 when the distal end has been placed in the surgical site at a location where it is desired to deliver the bone ingrowth enhancing material 30. Tool 160 may be very similar to a standard syringe, for example, but with an open bore at the distal end, so that the distal opening has an inside diameter the same, or only slightly smaller than the inside diameter of the tube 162. Other tools may be used for delivery of the bone ingrowth enhancing material, as would be readily apparent to one of ordinary skill in the biomechanical arts. The material can be spread using a spatula or other similar tool (not shown) if desired to facilitate further placement as desired. By filling the space with the material 30, it remains packed in place once the surgical site is closed.

Figure 11C:
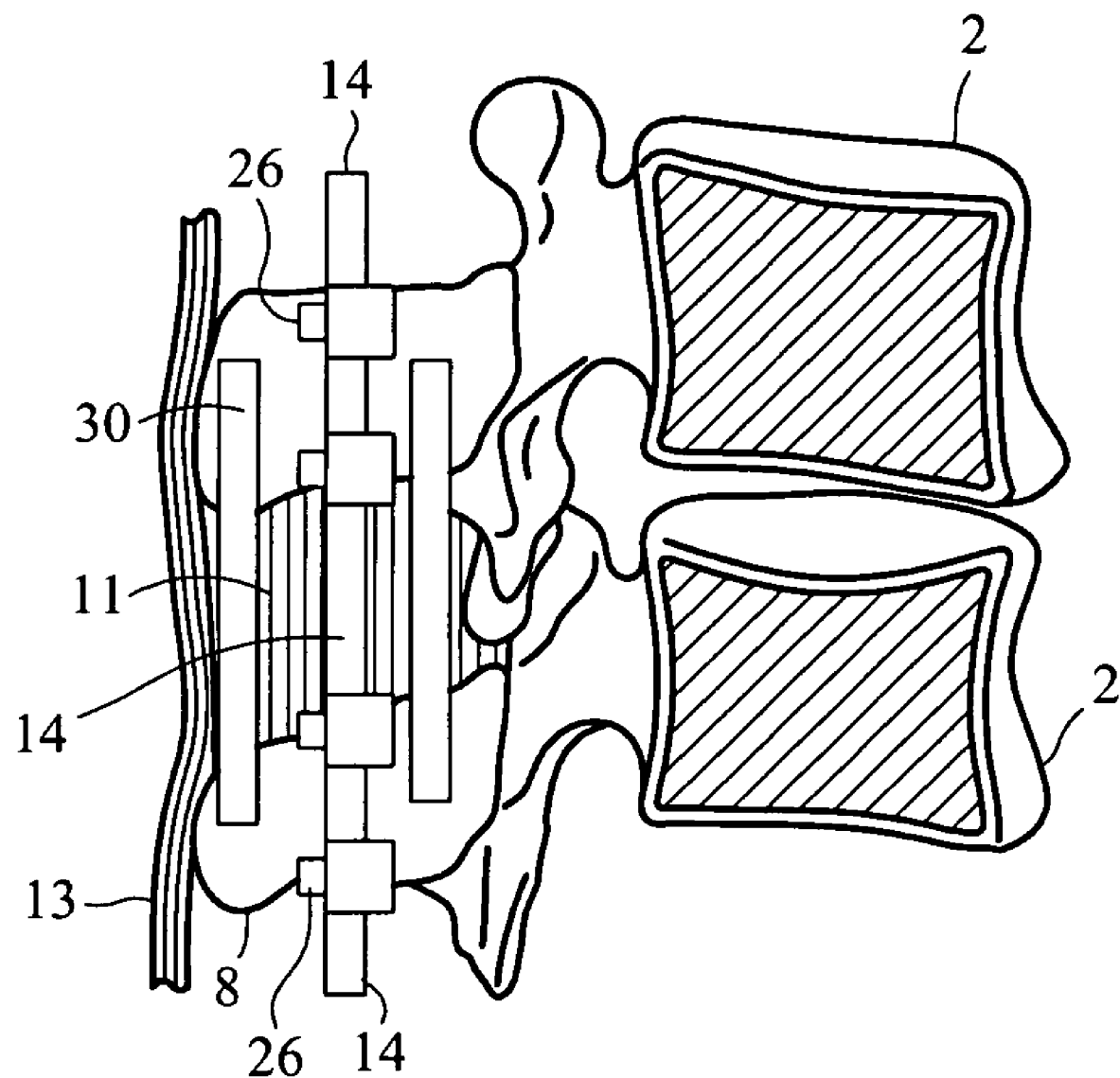
FIG. 11C illustration implantation of solid strips of bone ingrowth material after implantation of the device in FIG. 11A.

As noted previously, solid ingrowth materials 30, such as bone grafts, plates or the like may be implanted additionally, or alternatively to the particulate material, as illustrated in FIG. 11C. These solid materials may be adhered to the adjoining vertebra with adhesive, mechanically fixed thereto such as with screws or the like, and/or packed with a particulate bone ingrowth enhancing material 30 such as a type described with regard to FIG. 11B, for example. After completion of the implantation of the ingrowth enhancing material(s) 30, the site is closed around the materials, to maintain them relatively motionless to enhance the ingrowth of bone tissue therein.

Optionally, bone ingrowth enhancing material 30 may also be implanted, by opposite lateral sides of the device 10 and vertebrae 1, and this is particularly applicable when a bilateral device 10 has been implanted. The bone ingrowth enhancing material(s) 30 on the opposite side may be any of those described above with regard to the first side, and may be implanted according to any of the same techniques and in any of the same combinations described. Thus, the bone ingrowth material 30 placed on the opposite sides will typically be contacting and at least partially covering the device 10 on that side, as well as at least portions of the spinous processes 8 and/or laminae 7. The placement of the material may be performed using minimally invasive techniques, such as by using tool 160 for delivery of slurry or particulate material 30, with or without further spreading with a spatula or the like. Delivery of material 30 to both sides of the device 10 and vertebrae 1 can be performed from the single entry incision having been established at the beginning of the implantation procedure. Of course the lamina on the opposite side would also be exposed and would typically be prepared to facilitate a healing response such as with a high speed burr or the like, as described above.

After closure of the surgical site, device 10 maintains the spinal processes 8 a fixed distance apart, and by immobilizing the spinal processes by providing posterior fixation, this decreases spinal segment motion and allows bone ingrowth to occur to fuse the adjacent vertebrae and device 10 together.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A kit for treatment of spinal disorders, said kit comprising: a device including: a main body including a shaft having a longitudinal axis;
 a first clamping mechanism having first and second jaws configured to clamp a spinous process of a first vertebra;
 a second clamping mechanism having third and fourth jaws configured to clamp a spinous process of a second vertebra;
 said first, second, third and fourth jaws extending transversely from said main body, wherein at least two of said jaws are releasably mounted to said shaft and are mountable to and removable from said shaft by relative movement between said respective jaw and said shaft in a direction normal to a longitudinal axis of said shaft;
 wherein said at least two of said jaws each being connected at a first end to said shaft and having a free end opposite said first end when configured in said first or second clamping mechanism; and
 wherein said shaft has sufficient columnar strength to maintain distraction between the first and second vertebrae via said clamps, while also allowing at least one of the relative movements between the first and second vertebrae selected from the movements including lateral bending, flexion, extension and axial rotation; and
 a tool for inserting jaws of said clamping mechanisms, said tool including: an insertion arm having a distal end with a rotatable engagement feature configured to pass through a mating engagement feature on one of said jaws, and to be prevented from passing through said mating engagement feature after rotation about a longitudinal axis of said rotatable engagement feature; and
 a locking arm actuatable to rotate said rotatable engagement feature
 wherein said engagement feature has a first cross-sectional dimension along a first axis normal to a longitudinal axis of said insertion arm and a second cross-sectional dimension along an axis normal to said longitudinal axis, coplanar with said first axis, but extending in a different direction than a direction in which said first axis extends, and wherein said first cross-sectional dimension is greater than said second cross-sectional dimension.

2. The kit of claim 1, further comprising:

a tool for compressing jaws of said clamping mechanisms, said tool for compressing comprising:

first and second compressor arms having first and second distal tips formed with recesses configured and dimensioned to receive said shaft therein; and a pair of drive arms at a proximal end portion of said tool for compressing connected via a pivotal mount to said compressor arms and operable to drive said compressor arms toward each other when driving said drive arms toward each other.

3. The kit of claim 1, further comprising:

a tool for distracting said clamping mechanisms, said tool comprising:

first and second distractor arms having first and second distal tips formed with recesses configured and dimensioned to receive the shaft of the implant device therein; and a pair of drive arms at a proximal end portion of said tool connected via a pivotal mount to said distractor arms and operable to drive said distractor arms away from each other when driving said drive arms toward each other.

4. A kit for treatment of spinal disorders, said kit comprising: a device including:

a main body including a shaft having a longitudinal axis;

a first clamping mechanism having first and second jaws configured to clamp a spinous process of a first vertebra;

a second clamping mechanism having third and fourth jaws configured to clamp a spinous process of a second vertebra;

said first, second, third and fourth jaws extending transversely from said main body, wherein at least two of said jaws are releasably mounted to said shaft and are mountable to and removable from said shaft by relative movement between said respective jaw and said shaft in a direction normal to a longitudinal axis of said shaft;

wherein said at least two of said jaws each being connected at a first end to said shaft and having a free end opposite said first end when configured in said first or second clamping mechanism;

a component for facilitating fusion of the adjacent vertebrae while said device is implanted between the spinous processes; and a tool for inserting jaws of said clamping mechanisms, said tool including: an insertion arm having a distal end with a rotatable engagement feature configured to pass through a mating engagement feature on one of said jaws, and to be prevented from passing through said mating engagement feature after rotation about a longitudinal axis of said rotatable engagement feature; and a locking arm actuatable to rotate said rotatable engagement feature;

wherein said engagement feature has a first cross-sectional dimension along a first axis normal to a longitudinal axis of said insertion arm and a second cross-sectional dimension along an axis normal to said longitudinal axis, coplanar with said first axis, but extending in a different direction than a direction in which said first axis extends, and wherein said first cross-sectional dimension is greater than said second cross-sectional dimension.

5. The kit of claim 4, wherein said device further comprises a second shaft having a longitudinal axis, said second shaft being mountable to at least two of said jaws at distal end portions thereof, so that said second shaft is mounted on a side of the spinal processes that is opposite a side of the spinal processes that said first shaft is mounted on.

* * * * *